(12) United States Patent
Lee et al.

(10) Patent No.: US 10,578,621 B2
(45) Date of Patent: Mar. 3, 2020

(54) BIOMARKER PNCK FOR PREDICTING EFFECT OF A DUAL-TARGETING AGENT

(71) Applicant: Samsung Electronics Co., Ltd., Suwon-si, Gyeonggi-do (KR)

(72) Inventors: Ji Min Lee, Seoul (KR); Bo Gyou Kim, Seoul (KR); Kyung Ah Kim, Seongnam-si (KR); Seung Ja Oh, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 292 days.

(21) Appl. No.: 14/814,165

(22) Filed: Jul. 30, 2015

(65) Prior Publication Data
US 2016/0033518 A1    Feb. 4, 2016

(30) Foreign Application Priority Data
Jul. 30, 2014 (KR) .................. 10-2014-0097561

(51) Int. Cl.
*G01N 33/574*  (2006.01)
*C07K 16/30*  (2006.01)

(52) U.S. Cl.
CPC ....... *G01N 33/57496* (2013.01); *C07K 16/30* (2013.01); *C07K 2317/31* (2013.01); *C07K 2317/76* (2013.01); *G01N 2333/91205* (2013.01)

(58) Field of Classification Search
None
See application file for complete search history.

(56) References Cited

U.S. PATENT DOCUMENTS

| | | | |
|---|---|---|---|
| 6,486,170 B1 | 11/2002 | Hallahan et al. | |
| 6,524,832 B1 | 2/2003 | Kufe et al. | |
| 7,041,495 B2 | 5/2006 | Chodash et al. | |
| 7,070,968 B2 | 7/2006 | Kufe et al. | |
| 7,119,185 B2 | 10/2006 | Chodash et al. | |
| 7,368,113 B2 | 5/2008 | Chodash et al. | |
| 7,741,111 B2 | 6/2010 | Chodash et al. | |
| 7,838,512 B2 | 11/2010 | Kufe et al. | |
| 7,906,278 B2 | 3/2011 | Liew et al. | |
| 8,067,173 B2 | 11/2011 | Liew | |
| 8,080,377 B2 | 12/2011 | Ryu et al. | |
| 8,101,358 B2 | 1/2012 | Liew | |
| 8,110,358 B2 | 2/2012 | Liew | |
| 8,114,597 B2 | 2/2012 | Liew | |
| 8,133,674 B2 | 3/2012 | Liew | |
| 8,133,675 B2 | 3/2012 | Liew | |
| 8,148,072 B2 | 4/2012 | Liew | |
| 8,257,922 B2 | 9/2012 | Liew | |
| 8,258,284 B2 | 9/2012 | Liew et al. | |
| 8,563,696 B2 | 10/2013 | Cheong et al. | |

FOREIGN PATENT DOCUMENTS

| | | |
|---|---|---|
| KR | 2009-0121842 A | 11/2009 |
| KR | 2011-0047698 A | 9/2011 |
| WO | 1995-020960 | 8/1995 |

OTHER PUBLICATIONS

Deb et al (AJPCP, 300(C1139-C1154, 2011).*
Deb et al (AJPCP, 295(2):C365-C377, 2008).*
Tame (J. Comput. Aided Mol. Des. Mar. 1999; 13 (2): 99-108).*
Dixon (Proteins. 1997; Suppl 1: 198-204).*
Lensink et al. (Proteins. 2007; 69: 704-718).*
Prat et al (Biomed., 2:359-383, 2014).*
Mariuzza et al. (Annu. Rev. Biophys. Biophys. Chem. 1987; 16: 139-159).*
Gussow et al. (Methods in Enzymology. 1991; 203: 99-121).*

* cited by examiner

*Primary Examiner* — Brad Duffy
(74) *Attorney, Agent, or Firm* — Leydig, Voit & Mayer, Ltd.

(57) ABSTRACT

A biomarker PNCK for predicting an efficacy of a dual-targeting agent that targets both c-Met and EGFR and a method of predicting an effect of a dual-targeting agent that targets both c-Met and EGFR, selecting the subject for application of a dual-targeting agent that targets both c-Met and EGFR, or monitoring an effect of a dual-targeting agent that targets both c-Met and EGFR, including measuring a level of a PNCK and/or a PNCK coding gene.

10 Claims, 6 Drawing Sheets

Specification includes a Sequence Listing.

BIOMARKER PNCK FOR PREDICTING EFFECT OF A DUAL-TARGETING AGENT

CROSS-REFERENCE TO RELATED APPLICATIONS

This application claims the benefit of Korean Patent Application No. 10-2014-0097561 filed on Jul. 30, 2014 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 151,267 byte ASCII (Text) file named "721059_ST25.TXT," created Jul. 28, 2015.

BACKGROUND OF THE INVENTION

1. Field

The present disclosure relates to methods for predicting and monitoring efficacy of a dual-targeting agent that targets both c-Met and EGFR, methods for selecting a subject for application of the dual-targeting agent that targets both c-Met and EGFR, and methods for treating or preventing a cancer comprising administering the dual-targeting agent.

2. Description of the Related Art

A biomarker generally refers to a measured characteristic which may be used as an indicator of some change caused in an organism by an external factor. Active studies have recently been made to apply biomarkers to the diagnosis of various diseases, such as cancer, stroke, dementia, etc., and the prediction or monitoring of therapeutic effects of some agents. Among biomarkers relevant to drug development are pharmacodynamic markers (PD markers) for indicating whether drugs are functionally effective in vivo, and predictive markers for indicating the most likely response to particular drugs before administration. The use of such markers is helpful in establishing the clinical strategy of drugs. For example, a predictive marker, designed to indicate sensitivity or resistance to drug action, may be applied to the selection of patients to allow for more effective drug therapy while the action mode of a drug in individual patients can be monitored with a pharmacodynamic marker, which together can lead to the establishment of effective therapeutic strategies. Further, even in the absence of a predictive marker, a pharmacodynamic marker permits the early monitoring of responses to a drug, thus discriminating a drug-effective group from a drug-ineffective group in an early stage. Consequentially, more effective and successful drug therapies can be materialized. In addition, when applied to the monitoring of responses to a drug as a function of concentrations, a pharmacodynamic marker can be an index for calculating suitable doses of the drug.

Cancer is one of the leading causes of death. Although the development of medical techniques has brought about remarkable progress in cancer therapy, the 5-year survival rate has only improved by 10% over the past two decades. This is because cancer characteristics, such as rapid growth, metastasis, etc., make it difficult to diagnose and treat within a suitable time. The introduction of suitable biomarkers to cancer therapy would identify the characteristics of cancer to increase the opportunity of applying a suitable therapeutic in an optimal time, whereby cancer treatment could reach high success rates. For example, patients with lung cancer may differ from each other in cancer classification, genotype, and protein secretion, and thus must be treated with different, proper therapeutics. For chemotherapy using a specific drug, a corresponding biomarker, if present, would reduce the number of erroneous trials and increase the possibility of success. In this regard, it is very important to explore biomarkers for predicting or monitoring the effect of anti-cancer therapeutics. A proper biomarker, if successfully exploited, can make a great contribution to the utility and value of anti-cancer drugs and the success rate of treatment with them.

c-Met is a membrane receptor for hepatocyte growth factor (HGF) that possesses tyrosine kinase activity. HGF acts as a multi-functional cytokine which binds to the extracellular domain of c-Met to regulate cell division, cell motility, and morphogenesis in various normal and tumor cells c-Met is a proto-oncogene that takes part in a variety of mechanisms responsible for the development of cancer, such as oncogenesis, cancer metastasis, the migration and invasion of cancer cells, angiogenesis, etc., irrespectively of the ligand HGF, and thus has attracted intensive attention as a target for anti-cancer therapy. Actually, targeted therapies, such as antibodies against c-Met, have been continuously developed.

In order to increase the efficacy of therapies using c-Met-targeting drugs, it is required to develop biomarkers for predicting the effect of the c-Met-targeting drugs to select a subject who is suitable for application of the c-Met-targeting drugs, and/or for monitoring the responsiveness of a patient who has been treated with the c-Met-targeting drugs in order to establish more effective treatment strategies using the c-Met-targeting drugs.

BRIEF SUMMARY OF THE INVENTION

Provided are methods for predicting an efficacy of a dual-targeting agent that targets both c-Met and EGFR, or selecting a subject for application of a dual-targeting agent that targets both c-Met and EGFR. The methods comprise measuring the level of PNCK protein and/or the expression level of a PNCK encoding gene, detecting a mutation of PNCK or a PNCK encoding gene, and/or detecting a dysfunction of PNCK, in a biological sample from a patient. The methods further comprise determining that the dual-targeting agent is capable of exhibiting an effect in the biological sample, or selecting the patient for application of the dual-targeting agent, when the PNCK protein level or the expression level of a PNCK encoding gene in the biological sample is higher than that of a reference sample in which the dual-targeting agent has no effect, a mutation of PNCK or a PNCK coding gene is identified in the biological sample, and/or dysfunction of PNCK is present in the biological sample.

Also provided are methods for monitoring efficacy of a c-Met and EGFR dual-targeting agent. The methods comprise detecting a c-Met/EGFR/PNCK complex in a biological sample from a patient treated with a c-Met and EGFR dual-targeting agent, and detecting a c-Met/EGFR/PNCK complex in the biological sample. The c-Met and EGFR dual-targeting agent is determined to have efficacy if the c-Met/EGFR/PNCK complex is detected in the biological sample.

Further provided are methods of treating or preventing a cancer in a subject. The methods comprise administering to the subject a c-Met and EGFR dual-targeting agent, wherein the subject has a PNCK protein level or PNCK gene expression level that is higher than that of a reference sample in which the dual-targeting agent has no effect, wherein a mutation of PNCK or a PNCK coding gene is identified in the biological sample, and/or wherein dysfunction of PNCK is present in the biological sample.

Related methods and compositions also are provided.

DETAILED DESCRIPTION OF THE INVENTION

Figure 1:
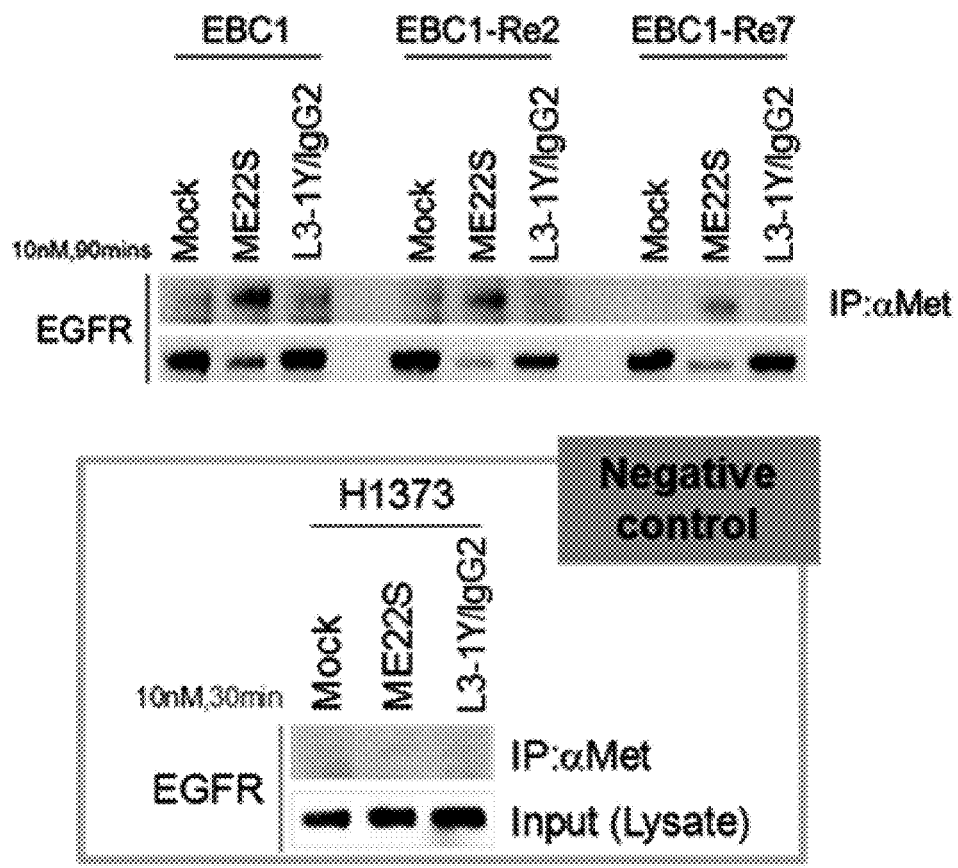
FIG. 1 displays western blotting results showing quantitative changes of c-Met and EGFR in EBC1 lung cancer cells when treated for 90 minutes with media containing 10 nM of an anti-c-Met antibody (L3-1Y/IgG2) or an anti-c-Met/anti-EGFR bispecific antibody (ME22S), indicating that the binding between c-Met and EGFR is increased by treating with an anti-c-Met/anti-EGFR bispecific antibody.

Provided herein is a method of predicting an efficacy of a dual-targeting agent that targets both c-Met and EGFR determining the efficacy of a c-Met and EGFR dual-targeting agent (e.g., an anti-c-Met/anti-EGFR bispecific antibody). The method comprises inducing binding between PNCK and a Met/EGFR complex. The method also comprises use of PNCK as a biomarker for predicting efficacy of the dual-targeting agent. In particular, it is observed that binding of Met/EGFR complex and PNCK is induced in cells on which a specific dual-targeting agent that targets both c-Met and EGFR exerts effects (i.e., which are responsive to a specific dual-targeting agent that targets both c-Met and EGFR). In addition, it is observed that even when resistance to a c-Met inhibitor, such as an anti-c-Met antibody, is induced, the dual-targeting agent can exhibit an anticancer effect by inducing binding of Met/EGFR complex and PNCK. In addition, when a quantitative increase of PNCK is involved in inducing a resistance to a c-Met inhibitor, such as an anti-c-Met antibody, the resistance can be overcome by a dual-targeting agent that targets both c-Met and EGFR having a PNCK-dependent activity.

The term "dual-targeting agent that targets both c-Met and EGFR" may refer to a composition or a compound, which targets both of c-Met and EGFR, and exhibits an effect of preventing, improving, alleviating, and/or treating a c-Met- and/or EGFR-associated disease, such as a cancer. For example, the effect of preventing, improving, alleviating, and/or treating a cancer may refer to a decrease in cancer cells or cancer tissues, a death of cancer cells or cancer tissues, an inhibition of cancer cell migration and/or invasion associated with cancer metastasis, and the like.

In an embodiment, the responsiveness to a dual-targeting agent that targets both c-Met and EGFR depends on the level and/or mutation and/or dysfunction of PNCK. In particular, when the level of PNCK or PNCK coding gene in a biological sample is high, a dual-targeting agent that targets both c-Met and EGFR, such as an anti-c-Met/anti-EGFR bispecific antibody, exhibits its desired effect on the biological sample or on a patient from whom the biological sample is isolated. In addition, innate or acquired resistance to a c-Met inhibitor (e.g., an anti-c-Met antibody) can be overcome by treating cancer cells demonstrating said resistance with the dual-targeting agent that targets both c-Met and EGFR, such as an anti-c-Met/anti-EGFR bispecific antibody, if the level in said cancer cells of PNCK or PNCK coding gene is relatively high, thereby generating an anticancer effect. In another embodiment, when PNCK or PNCK gene has a mutation and/or a dysfunction, a dual-targeting agent that targets both c-Met and EGFR (e.g., an anti-c-Met/anti-EGFR bispecific antibody) exhibits lower efficacy or has difficulty in overcoming resistance to a c-Met inhibitor, compared to the case with no mutation and/or dysfunction.

Measurement of the expression level and/or mutation and/or dysfunction of PNCK or its gene in a biological sample can provide information for predicting an efficacy of a dual-targeting agent that targets both c-Met and EGFR on the biological sample or a patient from who the biological sample is isolated or selecting a subject who is suitable for applying the dual-targeting agent that targets both c-Met and EGFR. In addition, when a resistance to a c-Met inhibitor such as an anti-c-Met antibody is present, the measurement of the expression level and/or mutation and/or dysfunction of PNCK or its gene in a biological sample can provide information for determining whether or not a dual-targeting agent that targets both c-Met and EGFR can achieve a desired anticancer effect. Based thereon, uses of PNCK as a biomarker for predicting and/or monitoring an efficacy of a dual-targeting agent that targets both c-Met and EGFR are provided.

PNCK (pregnancy-upregulated non-ubiquitous calmodulin kinase) is a negative regulator having a ligand-independent EGFR degradation activity, and thus, it can degrade EGFR without being stimulated by EGF ligand. PNCK may be from any mammal, for example, from a primate such as human, a monkey, and the like, a rodent such as a rat, a mouse, and the like, but not be limited thereto. For example, PNCK may be at least one selected from the group consisting of human PNCK (e.g., NCBI Accession No. NP_001034671.3, NP_001129212.1, etc.), mouse PNCK (e.g., NCBI Accession No. NP_001186280.1, NP_036170.1, etc.), rat PNCK (e.g., NCBI Accession No. NP_058971.1, etc.), and the like, but not be limited thereto. PNCK coding gene (mRNA) may be at least one selected from the group consisting of human PNCK gene (e.g., NCBI Accession No. NM_001039582.3, NM_001135740.1, etc.), mouse PNCK gene (e.g., NCBI Accession No. NM_001199351.1, NM_001199351.1, NM_012040.3, etc.), rat PNCK gene (e.g., NCBI Accession No. NM_017275.1, etc.), and the like, but not be limited thereto.

The dual-targeting agent that targets both c-Met and EGFR is useful for inducing binding of a c-Met/EGFR complex and a PNCK protein, to induce degradation of c-Met and EGFR, thereby exhibiting an effect (e.g., an anticancer effect) to treat a c-Met- and/or EGFR-associated disease, such as a cancer. PNCK is useful as a biomarker for predicting an efficacy of the dual-targeting agent. That is, the dual-targeting agent that targets both c-Met and EGFR exhibits a PNCK-dependent effect, thus, when the level of PNCK is high and/or there is no mutation and/or there is no dysfunction of PNCK, the dual-targeting agent that targets both c-Met and EGFR may have greater anti-cancer efficacy.

As used herein, the terms "efficacy" and "effect" of a dual-targeting agent refer to an anti-cancer effect (e.g., inhibition of cancer cell proliferation, etc.), anti-metastasis effect, and the like, particularly anti-cancer effect of the dual-targeting inhibitor, unless stated otherwise.

An embodiment provides a biomarker for predicting an efficacy of a dual-targeting agent that targets both c-Met and EGFR and/or selecting a subject for applying a dual-targeting agent that targets both c-Met and EGFR, comprising PNCK, PNCK coding gene, or a combination thereof.

Another embodiment provides a composition for predicting an efficacy of a dual-targeting agent that targets both c-Met and EGFR and/or selecting a subject for applying a dual-targeting agent that targets both c-Met and EGFR, comprising a substance interacting with PNCK, PNCK coding gene, modified PNCK, modified PNCK coding gene, or a combination thereof. Another embodiment provides a kit for predicting an efficacy of a dual-targeting agent that targets both c-Met and EGFR and/or selecting a subject for applying a dual-targeting agent that targets both c-Met and EGFR, comprising a substance interacting with PNCK, PNCK coding gene, modified PNCK, modified PNCK coding gene, or a combination thereof and a means for detecting the interaction between the substance and PNCK.

Another embodiment provides a composition for monitoring an efficacy of a dual-targeting agent that targets both c-Met and EGFR in a subject who is treated with the dual-targeting agent that targets both c-Met and EGFR, comprising a substance interacting with PNCK, PNCK coding gene, modified PNCK, modified PNCK coding gene, or a combination thereof. Another embodiment provides a kit for monitoring an efficacy of a dual-targeting agent that targets both c-Met and EGFR, comprising a substance interacting with PNCK, PNCK coding gene, modified PNCK, modified PNCK coding gene, or a combination thereof and a means for detecting the interaction between the substance and PNCK.

Another embodiment provides a method for predicting an efficacy of a dual-targeting agent that targets both c-Met and EGFR and/or selecting a subject for applying a dual-targeting agent that targets both c-Met and EGFR, comprising measuring the level and/or mutation of PNCK and/or PNCK coding gene, or a combination thereof, and/or a dysfunction of PNCK, in a biological sample.

As described above, the high level of PNCK and/or PNCK coding gene in a biological sample may indicate that PNCK, which is necessary for the activity of a dual-targeting agent to c-Met and EGFR, is present in the biological sample or a patient from which the biological sample is isolated, and thus, the dual-targeting agent to c-Met and EGFR will exert its desired effect well in the biological sample or a patient from which the biological sample is isolated. Therefore, in the method for predicting an efficacy of a dual-targeting agent to c-Met and EGFR or selecting a subject for applying a dual-targeting agent to c-Met and EGFR, when the level of at least one selected from the group consisting of PNCK and PNCK coding genes is high, it can be determined that a dual-targeting agent to c-Met and EGFR can exhibit an effect in the biological sample or a patient from which the biological sample is isolated, or the biological sample or a patient from which the biological sample is isolated can be determined as a subject suitable for applying a dual-targeting agent to c-Met and EGFR. Thus, the method for predicting an efficacy of a dual-targeting agent to c-Met and EGFR may further comprise, for example after the measuring step, determining (or predicting) that a dual-targeting agent to c-Met and EGFR exhibits an effect on the biological sample or a patient from which the biological sample is isolated, when the level of at least one selected from the group consisting of PNCK and PNCK coding genes is high. In addition, the method for selecting a subject for applying a dual-targeting agent to c-Met and EGFR may further comprise, for example after the measuring step, determining (or considering) the biological sample or a patient from which the biological sample is isolated as a subject suitable for applying a dual-targeting agent to c-Met and EGFR, when the level of at least one selected from the group consisting of PNCK and PNCK coding genes is high.

In addition, when any mutation of PNCK and/or PNCK coding gene or any dysfunction of PNCK and/or PNCK coding gene is not detected in a biological sample, it can be determined that PNCK with normal functions necessary for activity of a dual-targeting agent that targets both c-Met and EGFR is present in the biological sample, and thus, the dual-targeting agent that targets both c-Met and EGFR is predicted to exhibit a desired effect in the biological sample. Therefore, in the method for predicting an efficacy of a dual-targeting agent that targets both c-Met and EGFR or selecting a subject for applying a dual-targeting agent that targets both c-Met and EGFR, when there is no mutation or no dysfunction of PNCK and/or PNCK coding gene in a biological sample, it is determined (predicted) that the dual-targeting agent that targets both c-Met and EGFR can exhibit an effect in the biological sample or a patient from whom the biological sample is isolated, or that the biological sample or a patient from whom the biological sample is isolated is suitable for applying the dual-targeting agent that targets both c-Met and EGFR. Therefore, the method for predicting an efficacy of a dual-targeting agent that targets both c-Met and EGFR may further comprise, after the step of measuring mutation or dysfunction of PNCK and/or PNCK coding gene, i) determining (predicting) that the dual-targeting agent that targets both c-Met and EGFR can exhibit efficacy in the biological sample or a patient from whom the biological sample is isolated, when no mutation and/or no dysfunction of PNCK and/or PNCK coding gene is detected in a biological sample, or ii) determining (predicting) that the dual-targeting agent that targets both c-Met and EGFR cannot exhibit an effect in the biological sample or a patient from whom the biological sample is isolated, when a mutation and/or dysfunction of PNCK and/or PNCK coding gene is detected in a biological sample. In addition, the method for selecting a subject for applying a dual-targeting agent that targets both c-Met and EGFR may further comprise, after the step of measuring mutation or dysfunction of PNCK and/or PNCK coding gene, i) determining (predicting) that the biological sample or a patient from whom the biological sample is isolated is suitable for applying the dual-targeting agent that targets both c-Met and EGFR, when no mutation and/or no dysfunction of PNCK and/or PNCK coding gene is detected in a biological sample, or ii) determining (predicting) that the biological sample or a patient from whom the biological sample is isolated is not suitable for applying the dual-targeting agent that targets both c-Met and EGFR, when a mutation and/or dysfunction of PNCK and/or PNCK coding gene is detected in a biological sample.

In another embodiment, the method of predicting an efficacy of a dual-targeting agent that targets both c-Met and EGFR may further comprise, after the step of measuring the level, mutation and/or dysfunction of PNCK and/or PNCK coding gene, determining (predicting) that the dual-targeting agent that targets both c-Met and EGFR can exhibit efficacy in the biological sample or a patient from whom the biological sample is isolated, when the level of PNCK and/or PNCK coding gene is high and no mutation and/or no dysfunction of PNCK and/or PNCK coding gene is detected in a biological sample. In addition, the method of selecting a subject for applying a dual-targeting agent that targets both c-Met and EGFR may further comprise, after the step of measuring the level, mutation and/or dysfunction of PNCK and/or PNCK coding gene, determining (predicting) that the biological sample or a patient from whom the biological sample is isolated is suitable for applying the dual-targeting agent that targets both c-Met and EGFR, when the level of PNCK and/or PNCK coding gene is high and no mutation and/or no dysfunction of PNCK and/or PNCK coding gene is detected in a biological sample.

As used herein, the "high level of at least one selected from the group consisting of PNCK and PNCK coding gene" may be determined, when PNCK and/or PNCK gene is present, or the amount of at least one selected from the group consisting of PNCK and PNCK coding gene (DNA, cDNA, or mRNA) in a biological sample from a patient is higher than that in a reference sample. The term "reference sample" may refer to any biological material on which a dual-targeting agent that targets both c-Met and EGFR, such as an anti-c-Met/anti-EGFR bispecific antibody, has no effect. For example, the reference sample may be at least one selected from the group consisting of cell lines H1373 (ATCC, CRL-5866), HCC1806 (ATCC, CRL-2335), Caki-1 (ATCC, HTB-46), SKBR3 (ATCC, HTB-30), BT474 (ATCC, HTB-20), HT-29 (ATCC, HTB-38), LoVo (ATCC, CCL-229), HCT116 (ATCC, CCL-247), SW620 (ATCC, CCL-227), and Ls174T (ATCC, CL-188). The reference sample may comprise cells having resistance to a c-Met inhibitor and/or a dual-targeting agent that targets both c-Met and EGFR (e.g., cells acquiring a resistance to the c-Met inhibitor or the dual-targeting agent that targets both c-Met and EGFR by repeated and/or consistent administration thereof). In this case, the method may further comprise measuring the level of at least one selected from the group consisting of PNCK and PNCK coding gene, a mutation of at least one selected from the group consisting of PNCK and PNCK coding gene, a dysfunction of PNCK, or a combination thereof, in a reference sample, before the determining step. In addition, the method may further comprise comparing the level of PNCK and/or PNCK coding gene of the biological sample to that of the reference sample.

The level of PNCK may be determined by immunohistochemical staining using a general antibody (e.g., Cell signaling, #4874) against PNCK Immunohistochemical staining methods are routine for persons of ordinary skill in the art. Immunohistochemical staining is a method for identifying a material present in a cell or a tissue using antigen-antibody response, wherein a frozen or paraffin tissue section is generally used. A tissue section having a regular thickness is blocked for preventing non-specific binding of an antibody, and then, treated with a primary antibody. After a certain period, non-reacting primary antibody is removed, and the tissue section is treated with a secondary antibody. The secondary antibody attached tissue section can be detected using a streptavidin-attached material, such as streptavidin-HRP or streptavidin-alkaline phosphatase, which can bind to biotin attached to the secondary antibody. Most of the detecting responses are color reactions, which can be analyzed by a proper microscope. The staining may be scored on a scale ranging, e.g., '−', '0', '+1', '+2' or '+3,' wherein a score (stain intensity) of '−' or '0' represents no protein expression (no signal, negative), score of '+1' represents no or a slight protein expression (corresponding to a background signal), and scores of '+2' (strongly positive) to '+3' (very strongly positive) represent progressively increased levels of protein expression (the case showing the signal higher than '+3' is incorporated in the score of '+3') (the scores can be determined by a pathologist). Thus, when the score measured by immunohistochemical staining is "−", "0", or "+1", the level of PNCK may be determined as "negative", and when the score measured by immunohistochemical staining is greater than "+1" (i.e., "+2", or "+3"), the level of PNCK may be determined as "positive", where the "positive" may be understood as absence, or presence at a high level, of PNCK in the biological sample. Therefore, when the score measured by immunohistochemical staining using an antibody (e.g., Cell signaling, #4874) against PNCK is "+2", or "+3", it can be determined that "the level of at least one selected from the group consisting of PNCK and PNCK coding gene is high".

In another embodiment, when a mutation of PNCK and/or PNCK coding gene, and/or dysfunction of PNCK is detected (or identified) in the biological sample, it can be determined (or predicted) that a dual-targeting agent targeting both c-Met and EGFR cannot exert an effect on the biological sample or a patient from which the biological sample is isolated, compared to a reference sample comprising no mutation of PNCK and/or PNCK coding gene, and/or dysfunction of PNCK. The term "mutation of PNCK and/or PNCK coding gene" may refer to a deletion or substitution of at least one amino acid residue of an amino acid sequence of PNCK with another amino acid, or a modification of PNCK coding gene so that it encodes a modified PNCK having the deletion or substitution). The mutation of PNCK and/or PNCK coding gene may be a substitution of the amino acid residue Thr at position 171 of mouse PNCK (e.g., NCBI Accession No. NP_001186280.1, NP_036170.1, etc.) or rat PNCK (e.g., NCBI Accession No. NP_058971.1, etc.). In particular, the substitution of the amino acid residue Thr at position 171 of mouse PNCK (NP_001186280.1) or a species other than mouse (e.g., human), which corresponds to the position 171 of mouse PNCK determined by a general sequence alignment, with other amino acid. For example, the mutation of PNCK and/or PNCK coding gene may be the amino acid residue Thr at position 171 of mouse PNCK or an amino acid residue of a species other than mouse (e.g., human), which corresponds to the position 171 of mouse PNCK, with another amino acid, for example Ala (T171A), or modification of PNCK coding gene so as to encode the mutated PNCK, but not be limited thereto.

The mutation of PNCK or PNCK genes can be identified (or detected) by any general method for analyzing an amino acid sequence of a protein or a nucleotide sequence of a gene.

For example, the mutation of PNCK or PNCK genes can be identified (or detected) using a substance interacting with the mutated PNCK or the gene encoding the mutated PNCK. For example, the substance interacting with the mutated PNCK or the gene encoding the mutated PNCK may be at least one selected from the group consisting of chemicals (small molecular agent), antibodies, and aptamers, which interacts with the mutated PNCK, and primers, probes, and aptamers, which are capable of hybridizing with the gene encoding the mutated PNCK.

The mutation of PNCK and/or PNCK coding gene may be identified (or detected) using any general means for a gene or protein analysis assay. For example, the mutation of PNCK and/or PNCK coding gene may be identified (or detected) via an ordinary enzyme reaction, fluorescence, luminescence, and/or radioactivity detection using at least one selected from the group consisting of PNCK specific antibodies, and aptamers. More particularly, it may be identified (or detected) by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, polymerase chain reaction (PCR; e.g., qPCR, FISH (fluorescent in situ hybridization), microarray, and the like, but not be limited thereto.

The primer may be able to detect a gene fragment of about 5 to about 1000 bp, about 10 to about 500 bp, about 20 to about 200 bp, or about 50 to about 200 bp within the nucleotide sequence of a PNCK coding gene (full-length DNA, cDNA, or mRNA), and it may a primer pair each of which comprises or consists essentially of a nucleotide sequence hybridizable with (e.g., complementary to) a region of about 5 to about 100 bp, about 5 to about 50 bp, about 5 to about 30 bp, or about 10 to about 25 bp of the 3'-end and/or 5'-end of the gene fragment.

The probe or aptamer capable of hybridizing with the gene may comprise or consist essentially of a nucleotide sequence with a size from about 5 to about 100 bp, from about 5 to about 50 bp, from about 5 to about 30 bp, or from about 5 to about 25 bp, which is capable of hybridizing with (e.g., complementary to) a fragment (about 5 to about 100 bp, about 5 to about 50 bp, about 5 to about 30 bp, or about 5 to about 25 bp) of PNCK coding gene (full-length DNA, cDNA or mRNA). As used herein, the term "capable of hybridizing with" or "hybridizable with" may refer to that the primer, probe or aptamer has a sequence complementarity of 80% or higher, e.g., 90% or higher, 95% or higher, 98% or higher, 99% or higher, or 100%, with a specific region of a gene, thereby capable of complementarily binding to the specific region of the gene.

In the present disclosure, the mutation may a mutation leading to a dysfunction of PNCK. The a dysfunction of PNCK may be caused by the mutation of PNCK or PNCK coding gene, as described above (e.g. T171A in mouse PNCK), In the method of predicting an efficacy of a dual-targeting agent that targets both c-Met and EGFR and/or selecting a subject for applying a dual-targeting agent that targets both c-Met and EGFR, the measurement of a level of at least one selected from the group consisting of PNCK and PNCK coding gene in a biological sample may comprise i) applying (adding) a substance interacting with at least one selected from the group consisting of PNCK and PNCK coding gene to the biological sample; and ii) quantitatively analyzing the resulting reaction mixture to determine a level of at least one selected from the group consisting of PNCK and PNCK coding gene. In an embodiment, prior to the step i), a step of preparing a biological sample may be further performed, wherein the preparation step may comprise obtaining (isolating) a biological sample from the patient or obtaining a biological sample which has been isolated from a patient. In step i), the interacting substance, as described above, may be at least one selected from the group consisting of a chemical (small molecule), an antibody, an aptamer, all binding to PNCK, and a polynucleotide (e.g., a primer, a probe, an aptamer) binding to a part or entirety of a gene encoding PNCK, and optionally, may be conjugated with a label, such as a fluorescent or a coloring agent. The step i) may be configured to form a complex by applying (adding) the interacting substance to the biological sample. In step ii), the reaction mixture may be a complex resulting from interaction (binding) between at least one selected from the group consisting of PNCK and PNCK coding gene and the interacting substance, which can be obtained in step i). The quantitatively analyzing step may comprise quantifying the complex, the marker conjugated to the complex, or PNCK and/or PNCK coding gene segregated from the complex after the isolation of the complex from the biological sample. The quantitative analysis of PNCK may be performed by any general quantifying means of proteins, such as ELISA, immunohistochemistry, and the like, and the quantitative analysis of PNCK coding gene may be performed by any general quantifying means of genes (DNA or RNA), such as qPCR, mRNA microarray, and the like, but not limited thereto.

The level of PNCK and/or PNCK coding gene may be measured using any ordinary means for a gene or protein quantitative assay using a substance interacting with PNCK and/or PNCK coding gene. For example, the substance interacting with PNCK and/or PNCK coding gene may be at least one selected from the group consisting of chemicals (small molecules), proteins, peptides, nucleic acids (polynucleotides, oligonucleotides, etc.), and the like, which specifically interact with (or bind to) PNCK and/or PNCK coding gene. For example, the substance interacting with PNCK and/or PNCK coding gene may be at least one selected from the group consisting of chemicals, antibodies, and aptamers, which specifically bind to PNCK, and nucleic acids (e.g., primers, probes, aptamers, etc.) which bind to a whole or a part (e.g., about 5 to about 100 bp, about 5 to about 50 bp, about 5 to about 30 bp, or about 5 to about 25 bp) of PNCK coding gene.

For example, the level of PNCK may be measured via an ordinary enzyme reaction, fluorescence, luminescence, and/or radioactivity detection using at least one selected from the group consisting of PNCK specific antibodies, and aptamers. More particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray, and the like, but is not limited thereto.

In addition, the level of PNCK coding gene (full-length DNA, cDNA, or mRNA) may be measured by using any ordinary gene quantification methods including, but not limited to, an ordinary polymerase chain reaction (PCR; e.g., qPCR, qRT(reverse transcription)-PCR), FISH (fluorescent in situ hybridization), microarray, and the like, using a primer, probe, or aptamer, which is hybridizable with the gene. For example, the expression level of PNCK coding gene can be measured by measuring the level of PNCK mRNA e.g., using qRT-PCR. Methods for determining gene expression level in biological samples are routine for persons of ordinary skill in the art.

The primer may be able to detect a gene fragment of about 5 to about 1000 bp, about 10 to about 500 bp, about 20 to about 200 bp, or about 50 to about 200 bp within the nucleotide sequence of a PNCK coding gene (full-length DNA, cDNA, or mRNA), and it may a primer pair each of which comprises or consists essentially of a nucleotide sequence hybridizable with (e.g., complementary to) a region of about 5 to about 100 bp, about 5 to about 50 bp, about 5 to about 30 bp, or about 10 to about 25 bp of the 3'-end and/or 5'-end of the gene fragment.

The probe or aptamer capable of hybridizing with the gene may comprise or consist essentially of a nucleotide sequence with a size from about 5 to about 100 bp, from about 5 to about 50 bp, from about 5 to about 30 bp, or from about 5 to about 25 bp, which is capable of hybridizing with (e.g., complementary to) a fragment (about 5 to about 100 bp, about 5 to about 50 bp, about 5 to about 30 bp, or about 5 to about 25 bp) of PNCK coding gene (full-length DNA, cDNA or mRNA). As used herein, the term "capable of hybridizing with" or "hybridizable with" may refer to a primer, probe or aptamer having a sequence complementarity of 80% or higher, e.g., 90% or higher, 95% or higher, 98% or higher, 99% or higher, or 100%, with a specific region of a gene, thereby the primer, probe or aptamer being capable of binding to the specific region of the gene.

As used herein, the term "subject for applying a dual-targeting agent targeting both c-Met and EGFR" may refer to a patient to which administration of the dual-targeting agent that targets both c-Met and EGFR is suitable, and may include mammals such as rodents, e.g. mice, rats, etc.; and primates, e.g. humans, monkeys, etc. The patient may be a cancer patient. The biological sample may be the patient itself (e.g., a human, monkey, mouse, rat, etc.) or a cell, a tissue, or body fluid (e.g., blood, serum, urine, saliva, etc.) isolated from the patient or an artificial culture thereof. For example, the biological sample may be blood or serum.

The subject for applying a dual-targeting agent targeting both c-Met and EGFR may inherently have a high level of PNCK protein or PNCK coding gene (for example, PNCK mRNA), or have a high level of PNCK or PNCK coding gene due to acquiring a resistance to a c-Met inhibitor, such as an anti-c-Met antibody. Even when the subject acquires a resistance to a c-Met inhibitor, if the subject has a high level of PNCK or PNCK coding gene, the resistance can be overcome by administering a dual-targeting agent that targets both c-Met and EGFR, to obtain a desired effect.

In this case, the c-Met inhibitor may be at least one selected from the group consisting of an anti-c-Met antibody or an antigen-binding fragment thereof (e.g., as described below), crizotinib (PF-02341066; 3-((R)-1-(2,6-dichloro-3-fluorophenyl)ethoxy)-5-(1-(piperidin-4-yl)-1H-pyrazol-4-yl)pyridin-2-amine), cabozantinib (XL-184; N-(4-(6,7-dimethoxyquinolin-4-yloxy)phenyl)-N-(4-fluorophenyl)cyclopropane-1,1-dicarboxamide), foretinib (N-(3-fluoro-4-(6-methoxy-7-(3-morpholinopropoxy)quinolin-4-yloxy)phenyl)-N-(4-fluorophenyl)cyclopropane-1,1-dicarboxamide), PHA-665752((R,Z)-5-(2,6-dichlorobenzylsulfonyl)-3-((3,5-dimethyl-4-(2-(pyrrolidin-1-ylmethyl)pyrrolidine-1-carbonyl)-1H-pyrrol-2-yl)methylene)indolin-2-one), SU11274 ((Z)—N-(3-chlorophenyl)-3-((3,5-dimethyl-4-(1-methylpiperazine-4-carbonyl)-1H-pyrrol-2-yl)methylene)-N-methyl-2-oxoindoline-5-sulfonamide), SGX-523(6-(6-(1-methyl-1H-pyrazol-4-yl)-[1,2,4]triazolo[4,3-b]pyridazin-3-ylthio)quinoline), PF-04217903(2-(4-(3-(quinolin-6-ylmethyl)-3H-[1,2,3]triazolo[4,5-b]pyrazin-5-yl)-1H-pyrazol-1-yl)ethanol), EMD 1214063(Benzonitrile, 3-[1,6-Dihydro-1-[[3-[5-[(1-Methyl-4-Piperidinyl)Methoxy]-2-PyriMidinyl]Phenyl]Methyl]-6-Oxo-3-Pyridazinyl]), golvatinib (N-(2-fluoro-4-((2-(4-(4-methylpiperazin-1-yl)piperidine-1-carboxamido)pyridin-4-yl)oxy)phenyl)-N-(4-fluorophenyl)cyclopropane-1,1-dicarboxamide), INCB28060(2-fluoro-N-methyl-4-(7-(quinolin-6-ylmethyl)imidazo[1,2-b][1,2,4]triazin-2-yl)benzamide), MK-2461(N-((2R)-1,4-Dioxan-2-ylmethyl)-N-methyl-N'[3-(1-methyl-1H-pyrazol-4-yl)-5-oxo-5H-benzo[4,5]cyclohepta[1,2-b]pyridin-7-yl]sulfamide), tivantinib (ARQ 197; (3R,4R)-3-(5,6-Dihydro-4H-pyrrolo[3,2,1-ij]quinolin-1-yl)-4-(1H-indol-3-yl)pyrrolidine-2,5-dione), NVP-BVU972(6-[[6-(1-Methyl-1H-pyrazol-4-yl)imidazo[1,2-b]pyridazin-3-yl]methyl]quinoline), AMG458 ({1-(2-hydroxy-2-methylpropyl)-N-[5-(7-methoxyquinolin-4-yloxy)pyridin-2-yl]-5-methyl-3-oxo-2-phenyl-2,3-dihydro-1H-pyrazole-4-carboxamide}), BMS 794833 (N-(4-((2-amino-3-chloropyridin-4-yl)oxy)-3-fluorophenyl)-5-(4-fluorophenyl)-4-oxo-1,4-dihydropyridine-3-carboxamide), BMS 777607(N-[4-[(2-Amino-3-chloropyridin-4-yl)oxy]-3-fluorophenyl]-4-ethoxy-1-(4-fluorophenyl)-2-oxo-1,2-dihydropyridine-3-carboxamide), MGCD-265 (N-(3-Fluoro-4-(2-(1-methyl-1H-imidazol-4-yl)thieno[3,2-b]pyridin-7-yloxy)phenylcarbamothioyl)-2-phenylacetamide), AMG-208(7-Methoxy-4-[(6-phenyl-1,2,4-triazolo[4,3-b]pyridazin-3-yl)methoxy]quinoline), BMS-754807((2 S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-pyrrolidinecarboxamide), JNJ-38877605(6-[Difluoro[6-(1-methyl-1H-pyrazol-4-yl)-1,2,4-triazolo[4,3-b]pyridazin-3-yl]methyl]quinoline), and pharmaceutically acceptable salts thereof, or any combination thereof.

In an embodiment, the predicting, monitoring, or selecting method may further comprise administering the dual targeting agent to the patient or subject who is determined to be responsive to the dual targeting agent, to maintain the responsiveness to the dual-targeting agent after administration, or to be suitable for application of the dual-targeting agent, e.g., after determining step.

Another embodiment provides a method for inhibiting (or degrading) c-Met and EGFR, comprising administering a dual-targeting agent that targets both c-Met and EGFR to the selected subject dual-targeting agent that targets both c-Met and EGFR.

Another embodiment provides a method for preventing and/or treating a cancer, comprising administering a dual-targeting agent that targets both c-Met and EGFR to the selected subject for applying a dual-targeting agent that targets both c-Met and EGFR.

The method for inhibiting c-Met and EGFR or the method for preventing and/treating cancer may further comprise selecting a subject for applying a dual-targeting agent that targets both c-Met and EGFR, prior to the administering step. Details of the selection are as described above. The dual-targeting agent that targets both c-Met and EGFR may be an anti-c-Met/anti-EGFR bispecific antibody.

In an embodiment, the method for inhibiting c-Met and EGFR or for preventing and/or treating cancer may comprise of:

identifying (or selecting) a subject for applying a dual-targeting agent that targets both c-Met and EGFR; and administering a dual-targeting agent that targets both c-Met and EGFR to the subject, for example, at a pharmaceutically effective amount.

In another embodiment, the method for inhibiting c-Met and EGFR or for preventing and/or treating cancer may comprise of:

measuring the level of PNCK and/or PNCK coding gene in a biological sample, to select a subject who is suitable for applying a dual-targeting agent that targets both c-Met and EGFR; and administering a dual-targeting agent that targets both c-Met and EGFR to the selected subject, for example, at a pharmaceutically effective amount.

When a dual-targeting agent that targets both c-Met and EGFR is applied to a subject, c-Met and EGFR form a complex (c-Met/EGFR complex) mediated by the dual-targeting agent that targets both c-Met and EGFR, and PNCK binds to the formed complex, thereby inducing a degradation of c-Met and EGFR. That is, when a binding of c-Met/EGFR complex and PNCK is detected (i.e., a c-Met/EGFR/PNCK complex) in a biological sample from a subject who has been administered a dual-targeting agent that targets both c-Met and EGFR, it can be determined that the dual-targeting agent that targets both c-Met and EGFR is exhibiting efficacy in the subject. Therefore, a c-Met/EGFR/PNCK complex may be used as a marker for predicting and/or monitoring an efficacy of a dual-targeting agent that targets both c-Met and EGFR.

An embodiment provides a biomarker for monitoring an efficacy of a dual-targeting agent that targets both c-Met and EGFR, comprising a c-Met/EGFR/PNCK complex.

Another embodiment provides a composition and a kit for monitoring an efficacy of a dual-targeting agent that targets both c-Met and EGFR, comprising a substance interacting with a c-Met/EGFR/PNCK complex.

Another embodiment provides a method for predicting an efficacy of a dual-targeting agent that targets both c-Met and EGFR or selecting a subject suitable for applying a dual-targeting agent that targets both c-Met and EGFR, comprising detecting a c-Met/EGFR/PNCK complex in a biological sample. For example, the biological sample may be isolated from a patient to be administered the dual-targeting agent that targets both c-Met and EGFR. As described above, the detection of a c-Met/EGFR/PNCK complex (the presence of a c-Met/EGFR/PNCK complex) in the biological sample from a patient to be applied with the dual-targeting agent that targets both c-Met and EGFR may indicate that the dual-targeting agent that targets both c-Met and EGFR will exhibit an effect in the patient. Therefore, in the method for predicting or selecting, when a c-Met/EGFR/PNCK complex is detected in a biological sample isolated from a patient to be applied with the dual-targeting agent that targets both c-Met and EGFR, it can be determined that the dual-targeting agent that targets both c-Met and EGFR exhibits efficacy in the biological sample or the patient. Thus, the method for monitoring an efficacy of a dual-targeting agent that targets both c-Met and EGFR may further comprise, after the detecting step, determining that a dual-targeting agent that targets both c-Met and EGFR continues to exhibit efficacy in the biological sample or the patient, when a c-Met/EGFR/PNCK complex is detected in the biological sample isolated from a patient to be applied with the dual-targeting agent that targets both c-Met and EGFR.

Another embodiment provides a method for monitoring an efficacy of a dual-targeting agent that targets both c-Met and EGFR, comprising applying (contacting) a dual-targeting agent that targets both c-Met and EGFR to a biological sample and detecting a c-Met/EGFR/PNCK complex in the biological sample. For example, the biological sample applied with the dual-targeting agent that targets both c-Met and EGFR may be a biological sample obtained from a subject who has been administered a dual-targeting agent that targets both c-Met and EGFR. As described above, the detection of a c-Met/EGFR/PNCK complex (the presence of a c-Met/EGFR/PNCK complex) in the biological sample applied with the dual-targeting agent that targets both c-Met and EGFR may indicate that the dual-targeting agent that targets both c-Met and EGFR continues to exhibit an effect after application thereof. Therefore, in the method for monitoring an efficacy of a dual-targeting agent that targets both c-Met and EGFR, when a c-Met/EGFR/PNCK complex is detected in a biological sample applied with the dual-targeting agent that targets both c-Met and EGFR, it can be determined that the dual-targeting agent that targets both c-Met and EGFR continues to exhibit efficacy in the biological sample or the subject from whom the biological sample is obtained (or isolated) after application of the dual-targeting agent that targets both c-Met and EGFR. Thus, the method for monitoring an efficacy of a dual-targeting agent that targets both c-Met and EGFR may further comprise, after the detecting step, determining that a dual-targeting agent that targets both c-Met and EGFR continue to exhibit efficacy in the biological sample applied with the dual-targeting agent that targets both c-Met and EGFR or the subject from whom the biological sample is obtained, when a c-Met/EGFR/PNCK complex is detected in the biological sample applied with the dual-targeting agent that targets both c-Met and EGFR.

In the method for monitoring an efficacy of a dual-targeting agent that targets both c-Met and EGFR, the step of detecting a c-Met/EGFR/PNCK complex in the biological sample may comprise i) applying (adding) a substance interacting with a c-Met/EGFR/PNCK complex to the biological sample; and ii) quantitatively analyzing the resulting reaction mixture to determine a level of a c-Met/EGFR/PNCK complex. In an embodiment, prior to the step i), a step of preparing a biological sample may be further performed, wherein the preparation step may comprise obtaining (isolating) a biological sample from a subject or obtaining a biological sample which has been isolated from a subject. In step i), the interacting substance, as described above, may be at least one selected from the group consisting of chemicals (small molecules), proteins, peptides, nucleic acids (e.g., polynucleotides, oligonucleotides, etc.), capable of binding to a c-Met/EGFR/PNCK complex. For example, the interacting substance may be at least one selected from the group of chemicals (small molecules), antibodies, aptamers, and the like, which specifically recognize and/or bind to a c-Met/EGFR/PNCK complex, and optionally, may be conjugated with a label, such as a fluorescent or a coloring agent. The step i) may be configured to form a complex (of a c-Met/EGFR/PNCK complex and an interacting substance) by applying (adding) the interacting substance to the biological sample. In step ii), the reaction mixture may be a complex resulting from interaction (binding) between a c-Met/EGFR/PNCK complex and the interacting substance, which can be obtained in step i). The quantitatively analyzing step may comprise quantifying the complex, the marker conjugated to the complex, or a c-Met/EGFR/PNCK complex segregated from the c-Met/EGFR/PNCK complex and the interacting substance after the isolation of the c-Met/EGFR/PNCK complex and the interacting substance from the biological sample.

The detection of c-Met/EGFR/PNCK complex may be performed by any suitable protein analysis assay. For example, the detection of c-Met/EGFR/PNCK complex may be performed by an enzyme reaction, fluorescence, luminescence, and/or radioactivity detection, using at least one selected from the group consisting of c-Met/EGFR/PNCK complex specific antibodies, and aptamers. More particularly, the detection of c-Met/EGFR/PNCK complex may be performed by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray, and the like, but is not limited thereto.

The c-Met/EGFR/PNCK complex may be formed by binding of PNCK to EGFR in a c-Met/EGFR complex.

In application of a dual-targeting agent that targets both c-Met and EGFR, a high level of PNCK may increase the formation of a c-Met/EGFR/PNCK complex, thereby enhancing therapeutic efficacy of the dual-targeting agent. Therefore, the efficacy of a dual-targeting agent that targets both c-Met and EGFR can be more enhanced by increasing the level of PNCK in a cell. Thus, another embodiment provides a composition for enhancing an efficacy of a dual-targeting agent that targets both c-Met and EGFR, comprising at least one selected from the group consisting of PNCK protein and a PNCK expression stimulating substance (e.g., a PNCK gene, a recombinant vector containing a PNCK gene, a recombinant cell containing the recombinant cell, etc.). Another embodiment provides a method of enhancing an efficacy of a dual-targeting agent that targets both c-Met and EGFR, comprising administering at least one selected from the group consisting of a PNCK gene, a recombinant vector containing a PNCK gene, a recombinant cell containing the recombinant vector, to a subject in need of enhancing an efficacy of a dual-targeting agent that targets both c-Met and EGFR. The subject may be a patient who will be or has been administered with a dual-targeting agent that targets both c-Met and EGFR. The subject may be a cell, a tissue, or body fluid, isolated from said patient.

The "c-Met protein" refers to a receptor tyrosine kinase binding to hepatocyte growth factor. The c-Met proteins may be derived from any species, for example, those derived from primates such as human c-Met (e.g., NP_000236) and monkey c-Met (e.g., *Macaca mulatta*, NP_001162100), or those derived from rodents such as mouse c-Met (e.g., NP_032617.2) and rat c-Met (e.g., NP_113705.1). The proteins include, for example, a polypeptide encoded by the nucleotide sequence deposited under GenBank Accession Number NM_000245, or a protein encoded by the polypeptide sequence deposited under GenBank Accession Number NM_000236, or extracellular domains thereof. The receptor tyrosine kinase c-Met is involved in several mechanisms including cancer incidence, cancer metastasis, cancer cell migration, cancer cell penetration, angiogenesis, etc.

The "EGFR (epidermal growth factor receptor)" is a member of the HER family of receptor tyrosine kinases (RTKs). The binding of a ligand to the extracellular domain of EGFR induces receptor homo- or hetero-dimerization with other HER family receptors, which in turn results in intracellular self-phosphorylation of specific tyrosine residues within EGFP. EGFR self-phosphorylation leads to downstream signal transduction networks including MAPK and PI3K/Akt activation which affects cell proliferation, angiogenesis and metastasis. Overexpression, gene amplification, mutation, or rearrangement of EGFR are frequently observed in several human malignant tumors and are related to poor prognosis of cancer treatment and bad clinical outcomes. For such reasons, the EGFR is an important target in anticancer therapy. EGFR or HER2 may be derived from mammals, for example, primates such as humans and monkeys, or rodents such as rats and mice. For instance, the EGFR may be polypeptides encoded by the nucleotide sequences (mRNA) deposited under GenBank Accession Nos. JQ739160, JQ739161, JQ739162, JQ739163, JQ739164, JQ739165, JQ739166, JQ739167, NM_005228.3, NM_201284.1, NM_201282.1, or NM_201283.1.

As used herein, the term "dual-targeting agent that targets both c-Met and EGFR" may refer to any agent capable of simultaneously recognizing and/or binding to c-Met and EGFR, to degrade c-Met and EGFR, inhibit the expression of c-Met and EGFR, or inhibit the function of c-Met and EGFR. For example, the dual-targeting agent that targets both c-Met and EGFR may be an anti-c-Met/anti-EGFR bispecific antibody recognizing and/or binding to c-Met and EGFR at the same time. The anti-c-Met/anti-EGFR bispecific antibody may bind to c-Met and EGFR to induce the degradation thereof. In addition, the anti-c-Met/anti-EGFR bispecific antibody may induce binding between c-Met and EGFR to form a c-Met/EGFR complex, and/or binding between PNCK and a c-Met/EGFR complex to form a c-Met/EGFR/PNCK complex, and/or have a PNCK-dependent activity in the degradation of c-Met and EGFR, which is mediated by PNCK or the complex.

The anti-c-Met/anti-EGFR bispecific antibody may comprise a c-Met binding region and an EGFR binding region, and recognize and/or bind to c-Met and EGFR at the same time. In particular, the anti-c-Met/anti-EGFR bispecific antibody may comprise i) an EGFR binding region (for example, an anti-EGFR antibody or an antigen-binding fragment thereof, or an anti-EGFR antibody mimetic protein) and ii) an anti-c-Met antibody or an antigen-binding fragment thereof. The antigen-binding fragment thereof may be selected from the group consisting of scFv, (scFv)2, scFvFc, Fab, Fab', and F(ab')2. Alternatively, the anti-c-Met/anti-EGFR bispecific antibody may comprise i) an antibody mimetic protein specifically binding to EGFR (e.g., an anti-EGFR DARPin (designed ankyrin repeat protein)), and ii) an anti-c-Met antibody or an antigen-binding fragment thereof.

In a particular embodiment, the anti-EGFR antibody or an antigen-biding fragment may comprise:

at least one heavy chain complementarity determining region selected from the group consisting of CDR-H1 including the amino acid sequence of SEQ ID NO: 109, CDR-H2 including the amino acid sequence of SEQ ID NO: 110, and CDR-H3 including the amino acid sequence of SEQ ID NO: 111 or a heavy chain variable region including the at least one heavy chain complementarity determining region;

at least one light chain complementarity determining region selected from the group consisting of CDR-L1 including the amino acid sequence of SEQ ID NO: 112, CDR-L2 including the amino acid sequence of SEQ ID NO: 113, and CDR-L3 including the amino acid sequence of SEQ ID NO: 114 or a light chain variable region including the at least one light chain complementarity determining region;

a combination of the at least one heavy chain complementarity determining region and the at least one light chain complementarity determining region; or a combination of the heavy chain variable region and the light chain variable region.

For example, the anti-EGFR antibody or an antigen-binding fragment thereof may comprise or consist essentially of a heavy chain variable region including the amino acid sequence of SEQ ID NO: 115 or SEQ ID NO: 117, a light chain variable region including the amino acid sequence of SEQ ID NO: 116 or SEQ ID NO: 118, or a combination thereof.

TABLE 1

| | Heavy chain CDR | | Light chain CDR |
|---|---|---|---|
| CDR-H1 | NYDMS (SEQ ID NO: 109) | CDR-L1 | TGSSSNIGNNDVS (SEQ ID NO: 112) |
| CDR-H2 | GISHSSGSKYYADSVKG (SEQ ID NO: 110) | CDR-L2 | DDNKRPS (SEQ ID NO: 113) |
| CDR-H3 | KDATPRPLKPFDY (SEQ ID NO: 111) | CDR-L3 | GSWDASLNA (SEQ ID NO: 114) |

In a particular embodiment, the anti-EGFR antibody or an antigen-binding fragment thereof may be an anti-EGFR scFv including a heavy chain variable region including the amino acid sequence of SEQ ID NO: 115 or SEQ ID NO: 117, and a light chain variable region including the amino acid sequence of SEQ ID NO: 116 or SEQ ID NO: 118.

```
<SEQ ID NO: 115: a heavy chain variable region of
an anti-EGFR antibody >
EVQLLESGGGLVQPGGSLRLSCAASGFTFSNYDMSWVRQAPGKGLEWVSG

ISHSSGSKYYADSVKGRFTISRDNSKNTLYLQMNSLRAEDTAVYYCAKDA

TPRPLKPFDYWGQGTLVTVSS
(wherein the parts marked in bold type are CDR-H1,
CDR-H2, and CDR-H3 in order)

<SEQ ID NO: 116: a light chain variable region of
an anti-EGFR antibody >
QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGGGTKLTVLG
(wherein the parts marked in bold type are CDR-L1,
CDR-L2, and CDR-L3 in order)

<SEQ ID NO: 117: a heavy chain variable region of
an anti-EGFR antibody >
EVQLLESGGGLVQPGGSLRLSCAASGFTFSNYDMSWVRQAPGKCLEWVSG

ISHSSGSKYYADSVKGRFTISRDNSKNTLYLQMNSLRAEDTAVYYCAKDA

TPRPLKPFDYWGQGTLVTVSS
(wherein the parts marked in bold type are CDR-H1,
CDR-H2, and CDR-H3 in order)

<SEQ ID NO: 118: a light chain variable region of
an anti-EGFR antibody >
QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGCGTKLTVLG
(wherein the parts marked in bold type are CDR-L1,
CDR-L2, and CDR-L3 in order)
```

In another embodiment, the anti-EGFR antibody or an antigen-binding fragment thereof may be selected from the group consisting of cetuximab (Erbitux); panitumumab; an anti-EGFR antibody comprising a heavy chain variable region of SEQ ID NO: 121, a light chain variable region of SEQ ID NO: 123, or a combination thereof, or an antigen-binding fragment thereof an anti-EGFR antibody comprising a heavy chain variable region of SEQ ID NO: 125, a light chain variable region of SEQ ID NO: 126, or a combination thereof, or an antigen-binding fragment thereof.

In another embodiment, the EGFR binding region may be an anti-EGFR DARPin.

A DARPin (designed ankyrin repeat protein) is an antibody mimetic protein having high specificity and high binding affinity to a target protein, which is prepared via genetic engineering. DARPin is originated from natural ankyrin protein, and has a structure comprising at least 2, 3, 4, or 5 ankyrin repeat motifs. The DARPin can have any suitable molecular weight depending on the number of repeat motifs. For example, the DARPins comprising 3, 4 or 5 ankyrin repeat motifs may have a molecular weight of about 10 kDa, about 14 kDa, or about 18 kDa, respectively.

DARPin comprises a core element that provides structure and a target binding element that resides outside of the core element and binds to a target. The structural core comprises a conserved amino acid sequence and the target binding portion comprises an amino acid sequence that differs depending on the target. DARPin has target specificity similar to an antibody. Thus, a new form of a bispecific chimeric protein is provided by attaching DARPin to an antibody or antibody fragment, such as an IgG (e.g., IgG1, IgG2, IgG3 or IgG4) antibody, or an scFv-Fc antibody fragment, or the like.

The anti-EGFR DARPin (or EGFR-binding DARPin), which targets EGFR, may be any DARPin specifically binding to EGFR. For example, the anti-EGFR DARPin may be one selected from the group consisting of:

```
Anti-EGFR DARPin-01 (SEQ ID NO: 127):
dlgkklleaaragqddevrilmangadvnaddtwgwtplhlaayqghlei vevllkngadvnaydyigwtplhlaadghleivevllkngadvnasdyig dtplhlaahnghleivevllkhgadvnaqdkfgktafdisidngnedlae ilq Anti-EGFR DARPin-67 (SEQ ID NO: 128):
dlgkklleaaragqddevrilmangadvnatdndgntplhlsawighlei vevllkhgadvnaddllgmtplhlaadtghleivevllkygadvnardtr gktplhlaardghleivevllkhdadvnaqdkfgktafdisidngnedla eilq Anti-EGFR DARPin-68 (SEQ ID NO: 129):
dlgkklleaaragqddevrilmangadvnafdywgmtplhlaadnghlei vevllkhgadvnasdnfgftplhlaafyghleivevllkhgadvnafdmw gntplhlaaqnghleivevllkngadvnaqdkfgktafdisidngnedla eilq Anti-EGFR DARPin-69 (SEQ ID NO: 130):
dlgkklleaaragqddevrilmangadvnaddnagrtplhlaanfghlei vevllkngadvnakghhcntplhlaawaghleivevllkygadvnaddde gytplhlaadigdleivevllkygadvnawdmygrtplhlaasaghleiv evllkygadvnaqdkfgktafdisidngnedlaeilq
```

The anti-EGFR DARPin may comprise about 1 to about 10, about 1 to about 5, or about 1 to about 3 DARPin units, wherein the DARPin unit may comprise at least one selected from group consisting of SEQ ID NOs: 127 to 130. When anti-EGFR DARPin may comprise at least 2 DARPin units, the DARPin units may have the same or different amino acid sequence from each other.

In a polypeptide comprising a heavy chain variable region and a light chain variable region, an anti-EGFR scFv, or an anti-EGFR DARPin having at least two DARPin units, a heavy chain variable region, a light chain variable region, or each DARPin unit may be linked to each other with or without a linker. The linker may be a peptide liker, and if two or more linkers are used, the linkers may be the same or different from each other. The peptide linker may include 1 to 100 or 2 to 50 (e.g., 5 to 25, 1 to 10, or 2 to 5) amino acids, and the kinds of the amino acids included in the peptide linker may not have any limitation. For example, the peptide linker may include Gly, Asn and/or Ser residues, or may include neutral amino acids such as Thr and/or Ala. Amino acid sequences suitable for a peptide linker may be well known in the relevant art. The length of the peptide linker may be properly determined so that there is no negative effect on the function of the bispecific chimeric protein. For example, the peptide linker may include at least one amino acid selected from the group consisting of Gly, Asn, Ser, Thr, and Ala, wherein the total number of amino acids in the linker may be 1 to 100, 2 to 50, or 5 to 25. In one embodiment, the peptide linker may be represented as (GGGGS)n, wherein "n" is an integer from 1 to 10 (e.g., an integer from 2 to 5).

In an embodiment, the anti-c-Met antibody or an antigen-binding fragment thereof may be any antibody which specifically recognizes c-Met as an antigen and/or specifically binds to c-Met, or an antigen-binding fragment thereof. For example, the anti-c-Met antibody may be any antibody that acts on c-Met to induce intracellular internalization and degradation of c-Met, or antigen-binding fragment thereof. The anti-c-Met antibody may recognize any specific region of c-Met, e.g., a specific region in the SEMA domain, as an epitope.

"c-Met" or "c-Met protein" refers to a receptor tyrosine kinase (RTK) which binds hepatocyte growth factor (HGF). c-Met may be derived (obtained) from any species, particularly a mammal, for instance, primates such as human c-Met (e.g., GenBank Accession No. NP_000236), monkey c-Met (e.g., *Macaca mulatta*, GenBank Accession No. NP_001162100), or rodents such as mouse c-Met (e.g., GenBank Accession No. NP_032617.2), rat c-Met (e.g., GenBank Accession No. NP_113705.1), and the like. The c-Met protein may include a polypeptide encoded by the nucleotide sequence identified as GenBank Accession No. NM_000245, a polypeptide having the amino acid sequence identified as GenBank Accession No. NP_000236 or extracellular domains thereof. The receptor tyrosine kinase c-Met participates in various mechanisms, such as cancer incidence, metastasis, migration of cancer cells, invasion of cancer cells, angiogenesis, and the like.

c-Met may comprise three portions: extracellular, transmembrane, and intracellular. The extracellular portion comprises an α-subunit and a β-subunit which are linked to each other through a disulfide bond, and comprises a SEMA domain responsible for binding HGF, a PSI domain (plexin-semaphorins-integrin identity/homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third propellers within the epitopes of the SEMA domain. This region acts as an epitope for the anti-c-Met antibody.

The term "epitope," as used herein, refers to an antigenic determinant, a part of an antigen recognized by an antibody. In one embodiment, the epitope may be a region including 5 or more contiguous (consecutive on primary, secondary (two-dimensional), or tertiary (three-dimensional) structure) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide having 5 to 19 contiguous amino acids selected from among partial combinations of the amino acid sequence of SEQ ID NO: 71, wherein the polypeptide includes at least the amino sequence of SEQ ID NO: 73 (EEPSQ) which serves as an essential element for the epitope. For example, the epitope may be a polypeptide comprising the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third propellers within the SEMA domain of a c-Met protein. The epitope having the amino acid sequence of SEQ ID NO: 73 is a site to which the antibody or antigen-binding fragment according to one embodiment most specifically binds.

Thus, the dual-targeting agent that targets both c-Met and EGFR may specifically bind to an epitope which has 5 to 19 contiguous amino acids selected from the amino acid sequence of SEQ ID NO: 71, including SEQ ID NO: 73 (EEPSQ) as an essential element. For example, the dual-targeting agent that targets both c-Met and EGFR may specifically bind to an epitope including the amino acid sequence of SEQ ID NO: 71, SEQ ID NO: 72, or SEQ ID NO: 73.

In one embodiment, the dual-targeting agent that targets both c-Met and EGFR or an antigen-binding fragment thereof may comprise:

at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, SEQ ID NO: 2, or an amino acid sequence comprising 8-19 consecutive amino acids within SEQ ID NO: 2 including amino acid residues from the $3^{rd}$ to $10^{th}$ positions of SEQ ID NO: 2; and (c) a CDR-H3 comprising the amino acid sequence of SEQ ID NO: 6, SEQ ID NO: 85, or an amino acid sequence comprising 6-13 consecutive amino acids within SEQ ID NO: 85 including amino acid residues from the $1^{st}$ to $6^{th}$ positions of SEQ ID NO: 85, or a heavy chain variable region comprising the at least one heavy chain complementarity determining region;

at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, SEQ ID NO: 15, SEQ ID NO: 86, or an amino acid sequence comprising 9-17 consecutive amino acids within SEQ ID NO: 89 including amino acid residues from the $1^{st}$ to $9^{th}$ positions of SEQ ID NO: 89, or a light chain variable region comprising the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

```
            Formula I
                                    (SEQ ID NO: 4)
        Xaa₁-Xaa₂-Tyr-Tyr-Met-Ser,
``` wherein $Xaa_1$ is Pro, Ser, or is not present, and $Xaa_2$ is Glu or Asp,

```
            Formula II
                                    (SEQ ID NO: 5)
        Arg-Asn-Xaa₃-Xaa₄-Asn-Gly-Xaa₅-Thr,
``` wherein $Xaa_3$ is Asn or Lys, $Xaa_4$ is Ala or Val, and $Xaa_5$ is Asn or Thr,

```
            Formula III
                                    (SEQ ID NO: 6)
        Asp-Asn-Trp-Leu-Xaa₆-Tyr,
``` wherein $Xaa_6$ is Ser or Thr,

```
            Formula IV
                                    (SEQ ID NO: 7)
        Lys-Ser-Ser-Xaa₇-Ser-Leu-Leu-Ala-Xaa₈-Gly-Asn- Xaa₉-Xaa₁₀-Asn-Tyr-Leu-Ala
``` wherein $Xaa_7$ is His, Arg, Gln, or Lys, $Xaa_8$ is Ser or Trp, $Xaa_9$ is His or Gln, and $Xaa_{10}$ is Lys or Asn,

```
            Formula V
                                    (SEQ ID NO: 8)
        Trp-Xaa₁₁-Ser-Xaa₁₂-Arg-Val-Xaa₁₃
``` wherein $Xaa_{11}$ is Ala or Gly, $Xaa_{12}$ is Thr or Lys, and $Xaa_{13}$ is Ser or Pro, and

```
            Formula VI
                                    (SEQ ID NO: 9)
        Xaa₁₄-Gln-Ser-Tyr-Ser-Xaa₁₅-Pro-Xaa₁₆-Thr
``` wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may comprise an amino acid sequence selected from the group consisting of SEQ ID NOS: 1, 22, 23, and 24. The CDR-H2 may comprise an amino acid sequence selected from the group consisting of SEQ ID NOS: 2, 25, and 26. The CDR-H3 may comprise an amino acid sequence selected from the group consisting of SEQ ID NOS: 3, 27, 28, and 85.

The CDR-L1 may comprise an amino acid sequence selected from the group consisting of SEQ ID NOS: 10, 29, 30, 31, 32, 33, and 106. The CDR-L2 may comprise an amino acid sequence selected from the group consisting of SEQ ID NOS: 11, 34, 35, and 36. The CDR-L3 may comprise an amino acid sequence selected from the group consisting of SEQ ID NOS: 12, 13, 14, 15, 16, 37, 86, and 89.

In another embodiment, the antibody or antigen-binding fragment may comprise a heavy chain variable region comprising a polypeptide (CDR-H1) comprising an amino acid sequence selected from the group consisting of SEQ ID NOS: 1, 22, 23, and 24, a polypeptide (CDR-H2) comprising an amino acid sequence selected from the group consisting of SEQ ID NOS: 2, 25, and 26, and a polypeptide (CDR-H3) comprising an amino acid sequence selected from the group consisting of SEQ ID NOS: 3, 27, 28, and 85; and a light chain variable region comprising a polypeptide (CDR-L1) comprising an amino acid sequence selected from the group consisting of SEQ ID NOS: 10, 29, 30, 31, 32, 33 and 106, a polypeptide (CDR-L2) comprising an amino acid sequence selected from the group consisting of SEQ ID NOS: 11, 34, 35, and 36, and a polypeptide (CDR-L3) comprising an amino acid sequence selected from the group consisting of SEQ ID NOS 12, 13, 14, 15, 16, 37, 86, and 89.

In one embodiment of the dual-targeting agent that targets both c-Met and EGFR or antigen-binding fragment, the variable region of the heavy chain comprises the amino acid sequence of SEQ ID NO: 17, 74, 87, 90, 91, 92, 93, or 94 and the variable region of the light chain comprises the amino acid sequence of SEQ ID NO: 131, 18, 19, 20, 21, 75, 88, 95, 96, 97, 98, 99, or 107.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in terms of anti-isotype response compared to animal-derived antibodies, but the variable regions still comprise animal-derived amino acids, so that chimeric antibodies have side effects with respect to a potential anti-idiotype response. Humanized antibodies have been developed to reduce such side effects. Humanized antibodies are produced by grafting complementarity determining regions (CDR), which serve an important role in antigen binding, from non-human antibodies having the desired antigen specificity into a human antibody framework.

In using CDR grafting to produce humanized antibodies, choosing the human antibody framework is critical. Antibody databases, analysis of a crystal structure, and technology for molecule modeling are used to optimize the human antibody framework. However, even when the CDRs of animal-derived antibodies are grafted to the most optimized human antibody framework, in some cases, amino acids positioned in a framework of the animal-derived antibody and affecting antigen binding may be present. Therefore, in many cases, antigen binding affinity is not maintained, and thus application of additional antibody engineering technology for recovering the antigen binding affinity is necessary.

The anti c-Met antibodies may be, but are not limited to, animal antibodies (e.g., mouse-derived antibodies), chimeric antibodies (e.g., mouse-human chimeric antibodies), humanized antibodies, or human antibodies. The antibodies or antigen-binding fragments thereof may be isolated from a living body or non-naturally occurring. The antibodies or antigen-binding fragments thereof may be synthetic or recombinant. The antibody may be monoclonal.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, comprising a variable region, $V_H$, that comprises amino acid sequences sufficient to provide specificity to antigens. The heavy chain may further comprise three constant regions, $C_{H1}$, $C_{H2}$, and $C_{H3}$, and a hinge. The term "light chain" refers to a full-length light chain and fragments thereof, comprising a variable region, $V_L$, that comprises amino acid sequences sufficient to provide specificity to antigens. The light chain may further comprise a constant region, $C_L$.

The term "complementarity determining region (CDR)" refers to an amino acid sequence found in a hyper variable region of a heavy chain or a light chain of immunoglobulin. The heavy and light chains may respectively comprise three CDRs: CDRH1, CDRH2, and CDRH3; and CDRL1, CDRL2, and CDRL3. The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other.

The term "antigen-binding fragment" used herein refers to fragments of an intact immunoglobulin comprising portions of a polypeptide comprising antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, an Fab comprises light chain and heavy chain variable regions, a light chain constant region, and a first heavy chain constant region, $C_{H1}$, and has one antigen-binding site.

The Fab' fragment is different from the Fab fragment, in that Fab' further comprises a hinge region with at least one cysteine residue at the C-terminus of $C_{H1}$.

The F(ab')$_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv comprises a heavy chain variable region and a light chain variable region which are linked by a non-covalent bond. Single-chain Fv generally comprises a heavy chain variable region and a light chain variable region which are linked by a covalent bond via a peptide linker or linked at the C-terminals to have a dimer structure like the two-chain Fv. The peptide linker may be the same as described above, comprising, but not limited to, those having an amino acid length of 1 to 100, 2 to 50, particularly 5 to 25, and any kinds of amino acids may be included without any restrictions.

The antigen-binding fragments may be obtained using protease or by using a genetic recombination technique. For example, the Fab fragment may be obtained by restricted cleavage of a whole antibody with papain, and the F(ab')$_2$ fragment may be obtained by cleavage with pepsin.

The term "hinge region," as used herein, refers to a region between CH1 and CH2 domains within the heavy chain of an antibody which functions to provide flexibility for the antigen-binding site.

When an antibody undergoes a chimerization process, the IgG1 hinge of an antigen-specific antibody of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the dual-targeting agent that targets both c-Met and EGFR or an antigen-binding fragment thereof may be modified by any combination of deletion, insertion, addition, or substitution of at least one amino acid residue on the amino acid sequence of the hinge region so that it exhibits enhanced antigen-binding efficiency. For example, the antibody may comprise a hinge region comprising the amino acid sequence of SEQ ID NO: 100(U7-HC6), 101(U6-HC7), 102(U3-HC9), 103(U6-HC8), or 104 (U8-HC5), or a hinge region comprising the amino acid sequence of SEQ ID NO: 105 (non-modified human hinge). In particular, the hinge region has the amino acid sequence of SEQ ID NO: 100 or 101.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may comprise any of the antibodies defined in Korean Patent Publication No. 2011-0047698.

In the c-Met antibody or an antigen-binding fragment thereof, the remaining portion of the light chain and the heavy chain portion except the CDRs, the light chain variable region, and the heavy chain variable region as defined above, for example, the light chain constant region and the heavy chain constant region, may be from any subtype of immunoglobulin (e.g., IgA, IgD, IgE, IgG (IgG1, IgG2, IgG3, IgG4), IgM, and the like).

By way of further example, the anti-c-Met antibody or the antibody fragment may comprise:

a heavy chain comprising the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain comprising the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the 1$^{st}$ to 20$^{th}$ positions is a signal peptide), the amino acid sequence from the 21$^{st}$ to 240$^{th}$ positions of SEQ ID NO: 70, and the amino acid sequence of SEQ ID NO: 108.

For example, the dual-targeting agent that targets both c-Met and EGFR may be selected from the group consisting of:

an antibody comprising a heavy chain comprising the amino acid sequence of SEQ ID NO: 62 or the amino acid sequence from the 18$^{th}$ to 462$^{nd}$ positions of SEQ ID NO: 62 and a light chain comprising the amino acid sequence of SEQ ID NO: 68 or the amino acid sequence from the 21$^{st}$ to 240$^{th}$ positions of SEQ ID NO: 68;

an antibody comprising a heavy chain comprising the amino acid sequence of SEQ ID NO: 64 or the amino acid sequence from the 18$^{th}$ to 461$^{st}$ positions of SEQ ID NO: 64 and a light chain comprising the amino acid sequence of SEQ ID NO: 68 or the amino acid sequence from the 21$^{st}$ to 240$^{th}$ positions of SEQ ID NO: 68;

an antibody comprising a heavy chain comprising the amino acid sequence of SEQ ID NO: 66 or the amino acid sequence from the 18$^{th}$ to 460$^{th}$ positions of SEQ ID NO: 66 and a light chain comprising the amino acid sequence of SEQ ID NO: 68 or the amino acid sequence from the 21$^{st}$ to 240$^{th}$ positions of SEQ ID NO: 68;

an antibody comprising a heavy chain comprising the amino acid sequence of SEQ ID NO: 62 or the amino acid sequence from the 18$^{th}$ to 462$^{nd}$ positions of SEQ ID NO: 62 and a light chain comprising the amino acid sequence of SEQ ID NO: 70 or the amino acid sequence from the 21$^{st}$ to 240$^{th}$ positions of SEQ ID NO: 70;

an antibody comprising a heavy chain comprising the amino acid sequence of SEQ ID NO: 64 or the amino acid sequence from the 18$^{th}$ to 461$^{st}$ positions of SEQ ID NO: 64 and a light chain comprising the amino acid sequence of SEQ ID NO: 70 or the amino acid sequence from the 21$^{st}$ to 240$^{th}$ positions of SEQ ID NO: 70;

an antibody comprising a heavy chain comprising the amino acid sequence of SEQ ID NO: 66 or the amino acid sequence from the 18$^{th}$ to 460$^{th}$ positions of SEQ ID NO: 66 and a light chain comprising the amino acid sequence of SEQ ID NO: 70 or the amino acid sequence from the 21$^{st}$ to 240$^{th}$ positions of SEQ ID NO: 70;

an antibody comprising a heavy chain comprising the amino acid sequence of SEQ ID NO: 62 or the amino acid sequence from the 18$^{th}$ to 462$^{nd}$ positions of SEQ ID NO: 62 and a light chain comprising the amino acid sequence of SEQ ID NO: 108;

an antibody comprising a heavy chain comprising the amino acid sequence of SEQ ID NO: 64 or the amino acid sequence from the 18$^{th}$ to 461$^{st}$ positions of SEQ ID NO: 64 and a light chain comprising the amino acid sequence of SEQ ID NO: 108; and an antibody comprising a heavy chain comprising the amino acid sequence of SEQ ID NO: 66 or the amino acid sequence from the 18$^{th}$ to 460$^{th}$ positions of SEQ ID NO: 66 and a light chain comprising the amino acid sequence of SEQ ID NO: 108.

According to an embodiment, the dual-targeting agent that targets both c-Met and EGFR may comprise a heavy chain comprising the amino acid sequence from the 18$^{th}$ to 460$^{th}$ positions of SEQ ID NO: 66 and a light chain comprising the sequence from the 21$^{st}$ to 240$^{th}$ positions of SEQ ID NO: 68, or a heavy chain comprising the amino acid sequence from the 18$^{th}$ to 460$^{th}$ positions of SEQ ID NO: 66 and a light chain comprising the sequence of SEQ ID NO: 108.

The polypeptide of SEQ ID NO: 70 is a light chain comprising human kappa (κ) constant region. The polypeptide with the amino acid sequence of SEQ ID NO: 68 was obtained by replacing histidine at position 62 of SEQ ID NO: 70 with tyrosine. This histidine-to-tyrosine substitution may increase antibody production yield. The polypeptide with the amino acid sequence of SEQ ID NO: 108 is a polypeptide obtained by replacing serine at position 32 of SEQ ID NO: 68 (position 27e according to kabat numbering in the amino acid sequence from amino acid residues 21 to 240 of SEQ ID NO: 68; positioned within CDR-L1) with tryptophan. By such replacement, antibodies and antibody fragments comprising such sequences exhibit increased activities, such as c-Met binding affinity, c-Met degradation activity, and Akt phosphorylation inhibition.

In another embodiment, the dual-targeting agent that targets both c-Met and EGFR may include a light chain complementarity determining region comprising the amino acid sequence of SEQ ID NO: 106, a light chain variable region comprising the amino acid sequence of SEQ ID NO: 107, or a light chain comprising the amino acid sequence of SEQ ID NO: 108.

In an embodiment, the anti-c-Met/anti-EGFR bispecific antibody may comprise an anti-c-Met antibody or an antigen-binding fragment thereof, and an anti-EGFR antibody or an antigen-binding fragment thereof or an anti-EGFR DARPin, which is linked to the C-terminus or N-terminus, for example C-terminus, of the anti-c-Met antibody or the antigen binding fragment thereof.

In the anti-c-Met/anti-EGFR bispecific antibody, in order to fully perform the anti-c-Met antibody's activity to mediate intracellular migration and degradation of c-Met proteins, it may be advantageous that the anti-c-Met antibody has its own intact antibody structure. In addition, in case of the anti-EGFR antibody, its specific recognition and binding to EGFR is important, and thus it will be fine that just an antigen-binding fragment recognizing EGFR is included in the bispecific antibody. Therefore, the anti-c-Met/anti-EGFR bispecific antibody may be those comprising a complete form of an anti-c-Met antibody (e.g., IgG type antibody) and an antigen binding fragment of the anti-EGFR antibody linked to the C terminus of the anti-c-Met antibody (heavy chain).

In the anti-c-Met/anti-EGFR bispecific antibody, the anti-c-Met antibody or the antigen binding fragment thereof, and the anti-EGFR antibody or the antigen binding fragment thereof, may be linked via a peptide linker, or they may be linked directly and without a linker. Furthermore, a heavy chain portion and a light chain portion within the antigen binding fragment, for example, a heavy chain variable region and a light chain variable region within the scFv fragment, may be linked via a peptide linker or without a linker. The peptide linker which links the anti-c-Met antibody or the antigen binding fragment thereof and the anti-EGFR antibody or the antigen binding fragment thereof, and the peptide linker which links the heavy chain portion and the light chain portion within the antigen binding fragment, may be identical or different. The peptide linker may be include about 1 to about 100 amino acid residues, particularly about 2 to about 50, and any amino acid may be included without any restrictions. The peptide linker may include for example, Gly, Asn and/or Ser residues, and also include neutral amino acids such as Thr and/or Ala. Amino acid sequences suitable for the peptide linker may be those known in the pertinent art. Meanwhile, a length of the peptide linker may be variously determined within such a limit that the functions of the fusion protein will not be affected. For instance, the peptide linker may comprise a total of about 1 to about 100, about 2 to about 50, or about 5 to about 25 of one or more selected from the group consisting of Gly, Asn, Ser, Thr, and Ala. In one embodiment, the peptide linker may be represented as $(GGGS)_n$ (n is an integer of about 1 to about 10, particularly an integer of about 2 to about 5).

The dual-targeting agent that targets both c-Met and EGFR may be administered together with a pharmaceutically acceptable carrier. The composition as described above may further comprise a pharmaceutically acceptable carrier in addition to a dual-targeting agent that targets both c-Met and EGFR. The pharmaceutically acceptable carrier may be any one commonly used for the formulation of antibodies, which may be one or more selected from the group consisting of lactose, dextrose, sucrose, sorbitol, mannitol, starch, gum *acacia*, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The dual-targeting agent that targets both c-Met and EGFR may further comprise one or more selected from the group consisting of a lubricant, a wetting agent, a sweetener, a flavor enhancer, an emulsifying agent, a suspension agent, preservative, and the like.

The dual-targeting agent that targets both c-Met and EGFR may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in the stomach. In addition, the dual-targeting agent that targets both c-Met and EGFR may be administered using an optional device that enables an active substance to be delivered to target cells.

The term "the pharmaceutically effective amount" as used in this disclosure refers to an amount at which each active ingredient can exert pharmaceutically significant effects.

For one-time administration, a pharmaceutically effective amount of a dual-targeting agent that targets both c-Met and EGFR may be prescribed in a variety of ways, depending on many factors including formulation methods, administration manners, ages of patients, body weight, gender, pathologic conditions, diets, administration time, administration interval, administration route, excretion rate, and reaction sensitivity. For example, the effective amount for one-time administration of a dual-targeting agent that targets both c-Met and EGFR may comprise, but is not limited to, 0.001 to 100 mg/kg, or 0.02 to 10 mg/kg. The effective amount for one-time administration may be formulated into a single formulation in a unit dosage form or formulated in suitably divided dosage forms, or it may be manufactured to be contained in a multiple dosage container. For the kit, the effective amount of a dual-targeting agent that targets both c-Met and EGFR for one-time administration (single dose) may be contained in a package container as a base unit.

The dual-targeting agent that targets both c-Met and EGFR may be used for the prevention and/or treatment of a cancer and/or a cancer metastasis. The cancer may be associated with overexpression and/or abnormal activation of c-Met and/or EGFR. The cancer may be a solid cancer or a blood cancer. For example, the cancer may be but is not limited to at least one selected from the group consisting of squamous cell carcinoma, lung cancer, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophageal cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma, uterine carcinoma, salivary gland tumor, kidney cancer, prostate cancer, vulvar cancer, thyroid cancer, head and neck cancers, osteosarcoma, and brain cancer. The cancer may be a primary cancer or a metastatic cancer. The cancer may be resistant to a c-Met inhibitor, for example, an anti-c-Met antibody, a dual-targeting agent that targets both c-Met and EGFR, or an anti-c-Met/anti-EGFR bispecific antibody. The cancer may be a solid cancer such as gastric cancer, lung cancer, kidney cancer, and the like, which is resistant to a c-Met inhibitor, for example, an anti-c-Met antibody or an antigen-binding fragment thereof, a dual-targeting agent that targets both c-Met and EGFR, and/or an anti-c-Met/anti-EGFR bispecific antibody.

In addition, as described above, an efficacy of a dual-targeting agent that targets both c-Met and EGFR may be increased by the formation of a c-Met/EGFR/PNCK complex, and thus, the dual-targeting agent that targets both c-Met and EGFR may be administered together with PNCK and/or a PNCK stimulating substance. Therefore, an embodiment provides a pharmaceutical composition for treating and/or preventing a cancer and/or cancer metastasis, comprising a dual-targeting agent that targets both c-Met and EGFR and at least one selected from the group consisting of PNCK protein, PNCK gene, a recombinant vector containing the PNCK gene, and a recombinant cell containing the PNCK gene or the recombinant vector. Another embodiment provides a method of treating and/or preventing a cancer and/or cancer metastasis in a subject, comprising co-administering a dual-targeting agent that targets both c-Met and EGFR and at least one selected from the group consisting of PNCK protein, PNCK gene, a recombinant vector containing the PNCK gene, and a recombinant cell comprising the PNCK gene or the recombinant vector, to the subject. The co-administration may be performed simultaneously or sequentially in any order. The cancer is as described above. The cancer may be resistant to a c-Met inhibitor, for example, an anti-c-Met antibody, a dual-targeting agent that targets both c-Met and EGFR, or an anti-c-Met/anti-EGFR bispecific antibody. This method may be more effective when a PNCK protein and/or PNCK gene is absent or low and/or the expression of PNCK is inhibited.

The cancer prevention and/or treatment may comprise suppression of cancer cell growth, migration, invasion, and/or metastasis.

Another embodiment provides a pharmaceutical composition for treating a c-Met inhibitor resistant cancer or reducing a resistance to a c-Met inhibitor in a subject, comprising a dual-targeting agent that targets both c-Met and EGFR, for example, an anti-c-Met/anti-EGFR bispecific antibody. The pharmaceutical composition may further comprise at least one selected from the group consisting of PNCK protein, PNCK gene, a recombinant vector containing the PNCK gene, and a recombinant cell comprising the PNCK gene or the recombinant vector. Another embodiment provides a method of treating a c-Met-inhibitor-resistant cancer or reducing resistance to a c-Met inhibitor in a subject, comprising administering a dual-targeting agent that targets both c-Met and EGFR, for example, an anti-c-Met/ anti-EGFR bispecific antibody, to the subject. The method of treating a c-Met-inhibitor-resistant cancer or reducing resistance to a c-Met inhibitor may further comprise administering at least one selected from the group consisting of PNCK protein, PNCK gene, a recombinant vector containing the PNCK gene, and a recombinant cell comprising the PNCK gene or the recombinant vector to the subject, which may be performed simultaneously with, after, or before the step of administering a dual-targeting agent that targets both c-Met and EGFR. The subject may be one selected by the above described method for selecting a subject for applying a dual-targeting agent that targets both c-Met and EGFR. The cancer is as described above. The cancer may be resistant to a c-Met inhibitor, for example, an anti-c-Met antibody, a dual-targeting agent that targets both c-Met and EGFR, or an anti-c-Met/anti-EGFR bispecific antibody.

In this disclosure, the following effects are expected:

1) by the use of an anti-c-Met/anti-EGFR bispecific antibody, a desired effect can be obtained even on a patient who obtains no effect by pre-existing c-Met inhibitors;

2) an acquired resistance to a c-Met inhibitor can be overcome by the use of an anti-c-Met/anti-EGFR bispecific antibody which is capable of inducing binding between a c-Met-EGFR complex and PNCK;

3) the use of an EGFR targeting agent (e.g., a specific anti-c-Met/anti-EGFR bispecific antibody) having an activity of inducing binding between EGFR and PNCK, wherein the activity can be displayed independently from the presence of EGF ligand, can minimize side effects caused by activation of EGF ligand;

4) the acquisition of a resistance to a c-Met inhibitor can be monitored by the quantitative increase of PNCK; and 5) based on the understanding of an activity of a specific anti-c-Met/anti-EGFR bispecific antibody to induce a binding between a c-Met-EGFR complex and PNCK, a patient who can obtain an effect by the specific anti-c-Met/anti-EGFR bispecific antibody can be selected in advance, thereby increasing its therapeutic effect.

EXAMPLES

Hereafter, the present invention will be described in detail by examples.

The following examples are intended merely to illustrate the invention and are not construed to restrict the invention.

1.1. Production of "AbF46", a Mouse Antibody to c-Met 1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1{\sim}2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFv Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2, below.

TABLE 2

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5×10^5$ cells/ml, and after 24 hours, when the cell number reached to $1×10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of 5×10⁵ cells/ml, and after 24 hours, when the cell number reached to 1×10⁶ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA: light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was selected for the following examples, and name as L3-1Y/IgG2.

Reference Example 2: Preparation of an Anti-c-Met/Anti-EGFR Bispecific Antibody 2.1. Preparation of an Anti-EGFR scFv An anti-EGFR scFv binding to EGFR was prepared by inserting a peptide linker of $(GGGGS)_3$ between a heavy chain variable region of SEQ ID NO: 115 and a light chain variable region of SEQ ID NO: 116. In particular, the DNA sequence encoding a $(GGGGS)_3$ linker peptide was added to the DNA sequence (SEQ ID NO: 119) encoding the heavy chain variable region (SEQ ID NO: 115) and the DNA sequence (SEQ ID NO: 120) encoding the light chain variable region (SEQ ID NO: 116) of a humanized anti-EGFR antibody using an automatic gene synthesis (Bioneer Inc.) to synthesize a DNA fragment encoding a scFv of the anti-EGFR antibody. An anti-EGFR scFv prepared from the synthesized DNA fragment was named as "anti-EGFR antibody E-2".

The amino acid sequences of the heavy chain variable region and the light chain variable region of the prepared anti-EGFR scFv, and coding nucleotide sequences thereof are summarized in Table 4, as follows (wherein the sequences marked in bold type indicate CDRs, i.e., CDR-H1, CDR-H2, and CDR-H3, or CDR-L1, CDR-L2, and CDR-L3, in sequence):

TABLE 4

|  | Heavy chain variable region of anti-EGFR antibody E-2 | Light chain variable region of anti-EGFR antibody E-2 |
| --- | --- | --- |
| Amino acid sequence | EVQLLESGGGLVQPGGSLRLSCAASG FTFSNYDMSWVRQAPGKGLEWVSGI SHSSGSKYYADSVKGRFTISRDNSKN TLYLQMNSLRAEDTAVYYCAKDATP RPLKPFDYWGQGTLVTVSS (SEQ ID NO: 115) | QSVLTQPPSASGTPGQRVTISCTGSSS NIGNNDVSWYQQLPGTAPKLLIYDDN KRPSGVPDRFSGSKSGTSASLAISGLR SEDEADYYCGSWDASLNAYVFGGGT KLTVLG (SEQ ID NO: 116) |
| Coding nucleotide sequence | GAGGTGCAGCTGTTGGAGTCTGGGG GAGGCTTGGTACAGCCTGGGGGGTC CCTGAGACTCTCCTGTGCAGCCTCTG GATTCACCTTTAGCAATTATGATAT GAGCTGGGTCCGCCAGGCTCCAGGG AAGGGGCTGGAGTGGGTCTCAGGG ATCTCTCATAGTAGTGGTAGTAAA TATTACGCTGATTCTGTAAAGGT CGGTTCACCATCTCCAGAGACAATT CCAAGAACACGCTGTATCTGCAAAT GAACAGCCTGAGAGCCGAGGACAC GGCCGTGTATTACTGTGCGAAAGAT GCTACTCCGCGTCCGCTGAAGCCT TTCGACTACTGGGGCCAGGGTACA CTGGTCACCGTGAGCTCA (SEQ ID NO: 119) | CAGTCTGTGCTGACTCAGCCACCCT CAGCGTCTGGGACCCCCGGGCAGAG GGTCACCATCTCTTGTACTGGCTCT TCATCTAATATTGGCAATAATGAT GTCTCCTGGTACCAGCAGCTCCCAG GAACGGCCCCCAAACTCCTCATCTA TGATGATAATAAGCGGCCAAGCGG GGTCCCTGACCGATTCTCTGGCTCCA AATCTGGCACCTCAGCCTCCCTGGC CATCAGTGGGCTCCGGTCCGAGGAT GAGGCTGATTATTACTGTGGTTCTT GGGATGCTAGCCTGAATGCTTATG TCTTCGGCGGAGGCACCAAGCTGAC GGTCCTAGGC (SEQ ID NO: 120) |

A modified anti-EGFR scFv (heavy chain variable region: SEQ ID NO: 117 and light chain variable region: SEQ ID NO: 118) was prepared as described above, with the exception that the amino acid, G, at $44^{th}$ position of the heavy chain variable region (SEQ ID NO: 115) was substituted with C, and the amino acid, G, at $100^{th}$ position of the light chain variable region (SEQ ID NO: 116) was substituted with C. The amino acid location within the antibody complies with kabat numbering system. Such modifications (substitutions) can increase the stability of the anti-EGFR scFv.

<SEQ ID NO: 117: heavy chain variable region of
modified anti-EGFR antibody E-2>
EVQLLESGGGLVQPGGSLRLSCAASGFTFSNYDMSWVRQAPGKCLEWVSG

ISHSSGSKYYADSVKGRFTISRDNSKNTLYLQMNSLRAEDTAVYYCAKDA

TPRPLKPFDYWGQGTLVTVSS
(wherein the sequences marked in bold type indicate CDRs, i.e., CDR-H1, CDR-H2, and CDR-H3, in sequence)

<SEQ ID NO: 118: light chain variable region of
modified anti-EGFR antibody E-2>
QSVLTQPPSASGTPGQRVTISCTGSSSNIGNNDVSWYQQLPGTAPKLLIY

DDNKRPSGVPDRFSGSKSGTSASLAISGLRSEDEADYYCGSWDASLNAYV

FGCGTKLTVLG
(wherein the sequences marked in bold type indicate CDRs, i.e., CDR-L1, CDR-L2, and CDR-L3, in sequence)

The thus obtained modified anti-EGFR scFv (including SEQ ID NO: 117 and SEQ ID NO: 118) was used to manufacture the following bispecific antibodies.

2.2. Preparation of an Anti-c-Met/Anti-EGFR Bispecific Antibody

The modified anti-EGFR scFv (including SEQ ID NO: 117 and SEQ ID NO: 118) prepared in the above Reference Example 2.1 was fused at the c-terminal of Fc of the anti-c-Met antibody L3-1Y-IgG2 prepared in the above Reference Example 1. The fusion procedures are as follows.

A DNA segment having a base sequence (SEQ ID NO: 66) corresponding to the heavy chain of the anti-c-Met antibody L3-1Y-IgG2 prepared in above reference example 1 was inserted into a pcDNA™3.3-TOPO TA Cloning Kit (Cat no. 8300-01) which is included in OptiCHO™ Antibody Express Kit (Cat no. 12762-019) by Invitrogen Inc., and a DNA segment having a base sequence (SEQ ID NO: 68) corresponding to the light chain of the anti-c-Met antibody L3-1Y-IgG2 was inserted into a pOptiVEC™-TOPO TA Cloning Kit. Thereafter, the anti-EGFR scFv coding DNA prepared in Example 1 was fused at the c-terminal of Fc of L3-1Y-IgG2 inserted into pcDNA™3.3, using the coding DNA sequence of a linker peptide having 10 amino acid lengths consisting of (G4S)2, to construct vectors for the expression of bispecific antibodies.

The constructed vectors were each amplified using Qiagen Maxiprep kit (Cat no. 12662 and their temporary expressions were performed using Freestyle™ MAX 293 Expression System (invitrogen). A cell line used was 293 F cells, which were cultured in a suspension culture manner using FreeStyle™ 293 Expression Medium as a medium. One day before the temporary expression, the cells were prepared at a concentration of $5 \times 10^5$ cells/ml and after 24 hours, their temporary expression started when the number of the cells reached $1 \times 10^6$ cells/ml. Transfection was performed by a liposomal reagent method using Freestyle™ MAX reagent (invitrogen). DNA was prepared in a 15-ml tube in a ratio of heavy chain DNA:light chain DNA=3:2 and mixed with 2 ml of OptiPro™ SFM (invtrogen) (A), and 100 μl of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain each 100 ml of supernatants, which were then purified using AKTA Prime (GE healthcare). The culture was flowed at a flow rate of 5 ml/min. onto the AKTA Prime installed with Protein A column (GE healthcare, 17-0405-03) to perform elution using an IgG elution buffer (Thermo Scientific, 21004). The buffer was replaced by a PBS buffer to finally obtain purified bispecific anti-c-Met/anti-EGFR antibodies.

The thus prepared anti-c-Met/anti-EGFR bispecific antibody in which the modified anti-EGFR scFv is fused at the c-terminal of L3-1Y-IgG2 was named ME22S.

Example 1: Induction of Binding Between PNCK and c-Met/EGFR Complex by a Dual Targeting Agent to c-Met and EGFR Lung cancer cell line EBC1 (JCRB 0820) is a cell line on which anti-c-Met/anti-EGFR bispecific antibody ME22S exhibits an anticancer effect.

A western blotting experiment was conducted, to confirm that the formation of a Met/EGFR complex is induced by the treatment of ME22S to ME22S responsive EBC1 cell line. In particular, to examine whether or not a binding between Met and EGFR is induced in EBC1 cells by treatment of ME22S, a Met-EGFR complex (wherein Met and EGFR are bound to each other) was isolated and purified by co-immunoprecipitation, and quantified by immunoblotting. The cells were treated with the antibody (ME22S) for 90 minutes, and harvested and lysed by a lysis buffer Complete lysis-M (Roche, 04719956001), to obtain a protein extract. 500 μg of the extract was pulled-down together with anti-c-Met antibody-conjugated A/G agarose beads (Pierce), and subjected to an immunoblotting using an anti-EGFR antibody (Cell signaling), to identify the binding between Met and EGFR.

ME22S was treated at the fixed concentration of 10 nM for 90 minutes. For comparison, the same experiments were conducted for a L3-1Y/IgG2 treated group treated with L3-1Y/IgG2 instead of ME22S, and L3-1Y/IgG2 resistance acquired EBC1 cells treated with ME22S or L3-1Y/IgG2, wherein the L3-1Y/IgG2 resistance is acquired by repeatedly treating EBC1 cells with L3-1Y/IgG2. The L3-1Y/IgG2 resistance acquired EBC1 cells were prepared as follows: EBC1 (JCRB 0820) cells were treated with L3-1Y/IgG2 for 2 months with increasing the concentration thereof. The concentration of L3-1Y/IgG2 treated was increased from 1 ug/ml to 10 ug/ml until a resistance is induced. To confirm the acquisition of a resistance to L3-1Y/IgG2, the prepared clones were treated with L3-1Y/IgG2 at the concentration of 0 ug/ml, 0.016 ug/ml, 0.08 ug/ml, 0.4 ug/ml, or 2 ug/ml, and 72 hours after the antibody treatment, the number of the living cells was counted by CellTiter Glo assay (Promega, G7573). Clones where L3-1Y/IgG2 exhibits no effect were selected and named as EBC1-Re2 and EBC1-Re7, respectively. As a negative control, H1373 lung cancer cell line (ATCC, CRL-5866), on which ME22S exhibits no effect, was subjected to the same experiment, wherein ME22S was treated at the concentration of 10 nM for 30 minutes.

The obtained results are shown in FIG. 1. As shown in FIG. 1, Met-EGFR binding is increased in EBC1 by treating an anti-c-Met/anti-EGFR bispecific antibody.

To confirm that a binding between Met/EGFR complex and PNCK is induced by treating a ME22S-responsive EBC1 cells with ME22S, an immunoprecipitation using an anti-EGFR antibody was conducted and then a western blotting was conducted, to examine whether or not the proteins attached to beads include PNCK. In particular, to confirm whether or not a binding between PNCK and Met/EGFR complex was induced in EBC1 cells by treatment of ME22S, a PNCK-EGFR/Met complex (wherein PNCK and Met/EGFR complex are bound to each other) was isolated and purified by co-immunoprecipitation, and quantified by immunoblotting. EBC1 cells (JCRB 0820) were seeded on 60 mm plate at the amount of 5 ml (cell concentration: $2\times10^5$/ml) and cultured. 24 hours after, ME22S was treated for 30 minutes, 60 minutes, and 120 minutes, respectively. Then the cells were harvested and lysed with a lysis buffer Complete lysis-M (Roche, 04719956001) to obtain a protein extract. 500 µg of the extract was pulled-down together with anti-EGFR antibody-conjugated A/G agarose beads (Pierce), and subjected to an immunoblotting using an anti-PNCK antibody (Sigma Aldrich), to identify the binding between Met/EGFR complex and PNCK. The ME22S was treated at the fixed concentration of 10 nM for increased time, 30, 60, and 120 minutes.

Figure 2:
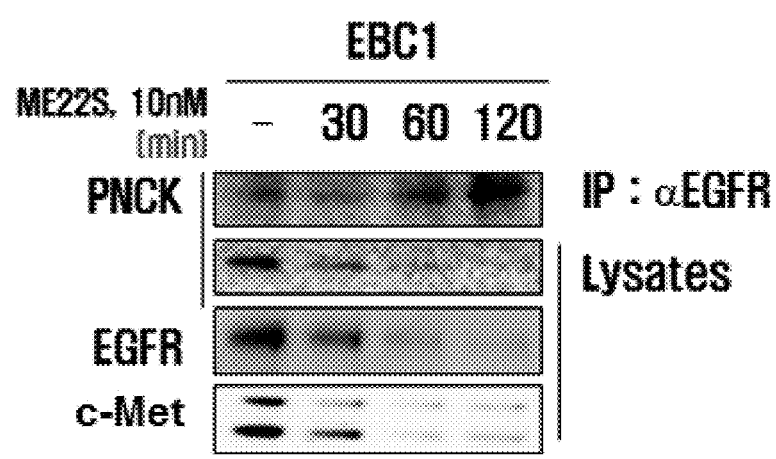
FIG. 2 displays western blotting results showing quantitative changes of PNCK and EGFR in EBC1 lung cancer cells when treated with an anti-c-Met/anti-EGFR bispecific antibody (ME22S), indicating that the binding between PNCK and EGFR is induced by treating with an anti-c-Met/anti-EGFR bispecific antibody.

The obtained results are shown in FIG. 2. As shown in FIG. 2, the binding between EGFR and PNCK is increased with increasing the treatment time of ME22S, indicating that PNCK binds to a Met/EGFR complex, the formation of which is confirmed in FIG. 1, through EGFR to form PNCK-EGFR/Met complex. In addition, FIG. 2 shows that PNCK interacts with the c-Met/EGFR complex upon treatment of cells with the bispecific antibody, ME22S, whereas EGFR and c-Met are gradually degraded with time.

Example 2: Induction of Binding Between PNCK and c-Met/EGFR Complex by a Dual Targeting Agent to c-Met and EGFR: In c-Met Inhibitor Resistant Cells To confirm the binding between Met/EGFR complex and PNCK in anti-c-Met antibody resistant cells wherein the resistance is induced by repeated treatment of an anti-c-Met antibody, EBC1 (JCRB 0820) cells were treated with L3-1Y/IgG2 repeatedly to prepare anti-c-Met antibody resistance acquired cells. EBC1 cells with no anti-c-Met antibody resistance (EBC1 parental cell) were responsive to L3-1Y/IgG2. The anti-c-Met antibody resistance acquired cells were prepared as follows: EBC1 (JCRB 0820) was treated with L3-1Y/IgG2 for at least 2 month with increasing the concentration. The concentration of L3-1Y/IgG2 was increased from 1 ug/ml to 10 ug/ml until a resistance is induced. To confirm the acquisition of a resistance to L3-1Y/IgG2, the prepared clones were treated with L3-1Y/IgG2 at the concentration of 0 ug/ml, 0.016 ug/ml, 0.08 ug/ml, 0.4 ug/ml, or 2 ug/ml, and 72 hours after the antibody treatment, the number of the living cells was counted by CellTiter Glo assay (Promega, G7573). Clones where L3-1Y/IgG2 exhibits no effect were selected and named as EBC1-Re7 (EBC1-L3-1Y/IgG2 resistant cell clone #7).

It was examined whether or not the binding between EGFR-Met complex and PNCK is induced by treating EBC1-Re7 cells with ME22S. In particular, to confirm the induction of a binding between Met/EGFR and PNCK in EBC1-L3-1Y/IgG2 resistant cell clone #7 cells (indicated as "EBC1-Re7"; see Example 4) by treatment of ME22S, a PNCK-EGFR/Met complex (wherein PNCK and Met/EGFR complex are bound to each other) was isolated and purified by co-immunoprecipitation, and quantified by immunoblotting. EBC1-Re7 cells were seeded on 60 mm plate at the amount of 5 ml (cell concentration: $2\times10^5$/ml) and cultured. 24 hours after, ME22S was treated at the concentration of 10 nM for 30 minutes. Then the cells were harvested and lysed with a lysis buffer Complete lysis-M (Roche, 04719956001) to obtain a protein extract. 500 µg of the extract was pulled-down together with anti-EGFR antibody-conjugated A/G agarose beads (Pierce), and subjected to an immunoblotting using an anti-PNCK antibody (Sigma Aldrich), to identify the binding between Met/EGFR complex and PNCK.

Figure 3:
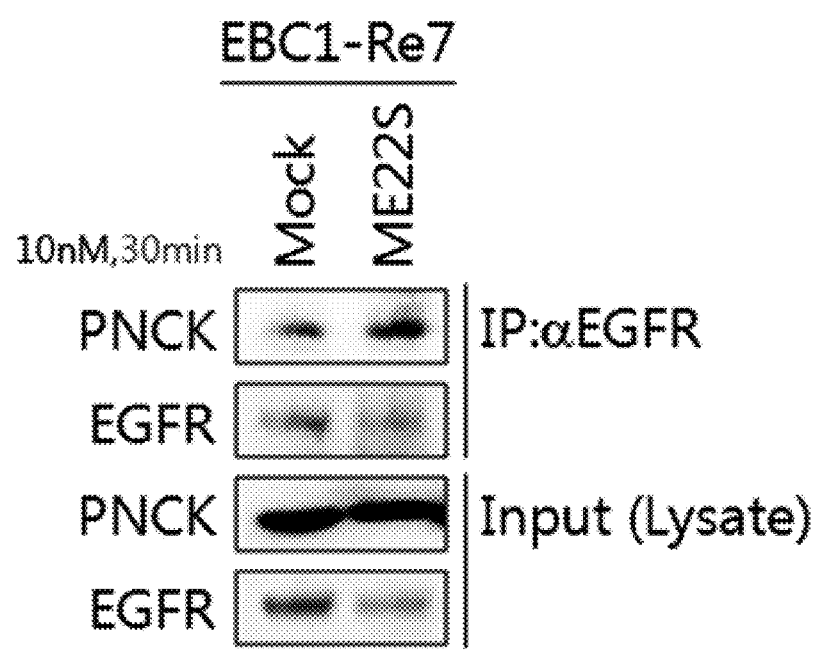
FIG. 3 displays western blotting results showing quantitative changes of PNCK and EGFR in EBC1 lung cancer cells resistant to an anti-c-Met antibody when treated with an anti-c-Met/anti-EGFR bispecific antibody, indicating that the binding between PNCK and EGFR is induced by treating an anti-c-Met/anti-EGFR bispecific antibody even in anti-c-Met antibody-resistant cells.

The obtained results are shown in FIG. 3. As shown in FIG. 3, the binding between a EGFR-Met complex and PNCK is induced in the resistance acquired EBC1-Re7 cells by treatment of ME22S, similar to EBC1 cells with no resistance.

Example 3: Decreased EGFR Degradation Effect of ME22S in PNCK Expression Inhibited EBC1 Cells It was confirmed that the EGFR degradation effect of ME22S in EBC1 lung cancer cells, when the level of PNCK is decreased by inhibiting the expression of PNCK using siRNA. Since EBC1 lung cancer cell line has relatively high level of PNCK protein, the anticancer effect on the cells was conducted by knocking-down PNCK gene using siRNA.

5000 cells of EBC1 lung cancer cell line (JCRB 0820) was transfected with a control siRNA (indicated as "siCTL"; using SMARTpool of Dharmacon, catalog number: D-001206-14-20) or PNCK siRNA (indicated as "siPNCK"; using SMARTpool of Dharmacon, catalog number: L-027176-00-0010), and then seeded on 96-well plate and cultures (medium: 10% FBS in RPMI 1640 (GIBCO), Temperature: 37° C.). The transfection was conducted using lipofectamine RNAi max (Invitrogen). The transfection was conducted by pre-incubating 10~20 uM of siRNA diluted in opti-MEM (Gibco) and lipofectamine RNAi max diluted in opti-MEM (Gibco) at room temperature for 15 minutes, and mixing the pre-incubated product with 5000 cells/well of each cell line. 24 hours after, the reverse transfected cells were treated with ME22S or L3-1Y/IgG2 at the concentration of 10 nM for 90 minutes. Then, EGFR was detected by western blotting. The degrees of EGFR degradation by ME22S and L3-1Y/IgG2 were respectively measured and compared to each other, and cells treated with medium only were used as a negative control. In this example, the efficacy of antibodies was examined by determining the increase/decrease of the total amount of EGFR based on the fact that the antibody binds to EGFR displayed on cell surface, induces internalization into a cell, and degrades EGFR.

Figure 4:
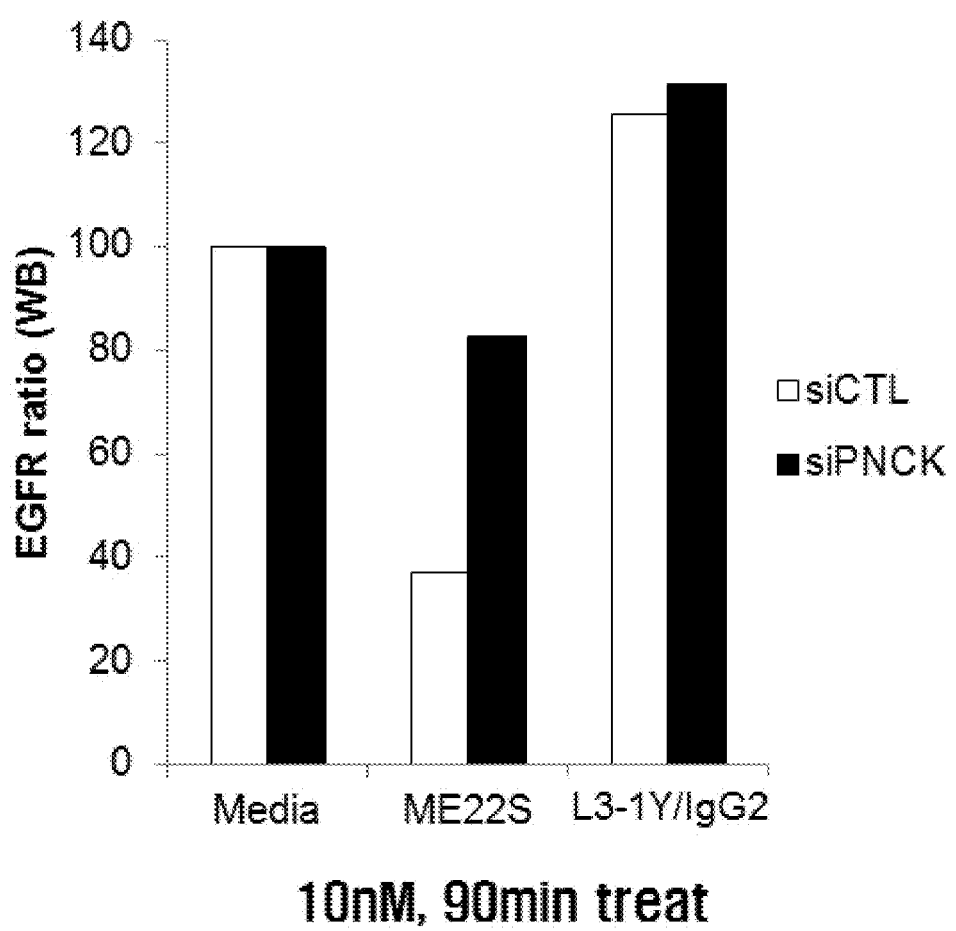
FIG. 4 is a graph showing the degree of degradation of EGFR in PNCK expression-suppressed EBC1 lung cancer cells by an anti-c-Met antibody or an anti-c-Met/anti-EGFR bispecific antibody, indicating that when the expression of PNCK is suppressed, the EGFR degradation activity of an anti-c-Met/anti-EGFR bispecific antibody is decreased, wherein siCTL refers to control siRNA having no target, siPNCK refers to PNCK siRNA, and EGFR ratio refers to a relative amount in each antibody-treated sample of EGFR to that of antibody non-treated sample ("Media").

EBC1 cells were seeded at the amount of $2\times10^5$ cells/ml, and after culturing for 24 hours, the cells were treated with each antibody at the concentration of 10 nM. After further culturing for 90 minutes, the cells treated with antibody were lysed using a lysis buffer. The lysis buffer used was Complete lysis-M (Roche, 04719956001). The determined EGFR weight was quantified as an EGFR ratio through ImageJ program. The obtained results were shown in FIG. 4. As shown in FIG. 4, when treating siCTL, ME22S exhibits EGFR degradation effect well, whereas when the level of PNCK is decreased by siPNCK, ME22S does not exhibit EGFR degradation effect. These results indicate that ME22S exhibits no or poor anticancer effect when the expression of PNCK is inhibited.

Example 4: Measurement of the Level of PNCK in Anti-c-Met Antibody Resistance Acquired Cell Line To examine the quantitative change of PNCK when a resistance to an anti-c-Met antibody is induced, L3-1Y/IgG2 resistance acquired cell lines were prepared by repeatedly treating EBC1 (JCRB 0820) and H1993 (ATCC, CRL-5909)

cells with L3-1Y/IgG2. Both of the two cells (parent cell) were all responsive to L3-1Y/IgG2, before inducing L3-1Y/IgG2 resistance. The L3-1Y/IgG2 resistance acquired cell lines were prepared as follows: each of EBC1 (JCRB 0820) and H1993 (ATCC, CRL-5909) cell lines was treated with L3-1Y/IgG2 for at least 2 months, with increasing the concentration of treated antibody. The concentration of L3-1Y/IgG2 was increased from 1 ug/ml to 10 ug/ml until a resistance is induced. To confirm the acquisition of a resistance to L3-1Y/IgG2, the prepared clones were treated with L3-1Y/IgG2 at the concentration of 0 ug/ml, 0.016 ug/ml, 0.08 ug/ml, 0.4 ug/ml, or 2 ug/ml, and 72 hours after the antibody treatment, the number of the living cells was counted by CellTiter Glo assay (Promega, G7573). Clones where L3-1Y/IgG2 exhibits no effect were identified.

The obtained L3-1Y/IgG2 resistance acquired cell lines were named as EBC1-Re7 (EBC1-L3-1Y/IgG2 resistant cell clone #7), H1993-Re9 (H1993-L3-1Y/IgG2 resistant cell clone #9), and H1993-Re21(H1993-L3-1Y/IgG2 resistant cell clone #21), respectively.

The PNCK level in the resistance acquired cells was measured. Each of EBC1, EBC1-Re7, H1993, H1993-Re9, and H1993-Re21 cells was seeded on 60 mm plate at the amount of 5 ml (cell concentration: $2 \times 10^5$/ml) and cultured. 24 hours after, then the cells were lysed using buffer Complete lysis-M (Roche, 04719956001) to obtain a protein extract therefrom. The PNCK level was measured by western blotting.

Figure 5:
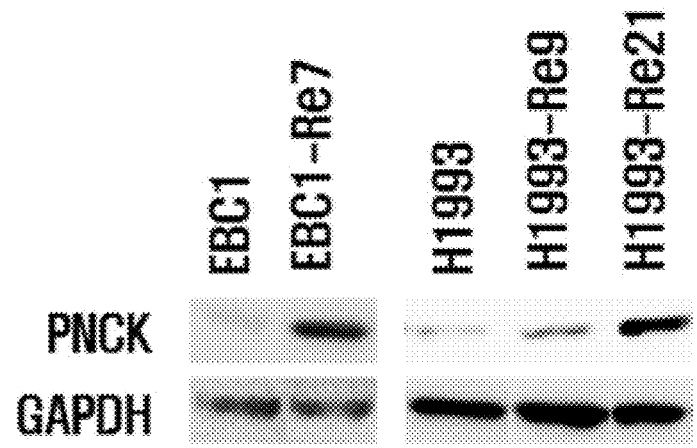
FIG. 5 displays western blotting results showing the change in the PNCK level in EBC1 and H1993 lung cancer cell lines and those that have acquired resistance to an anti-c-Met antibody (EBC1-Re7, H1993-Re9, and H1993-Re21), indicating that the acquisition of a resistance to an anti-c-Met antibody leads to increase in the PNCK level.

The measured amount of the protein was compared to a parent cell which is a cell before acquisition of resistance, and the results are shown in FIG. 5. In FIG. 5, GAPDH (housekeeping gene) was used as a control. As shown in FIG. 5, the PNCK level was considerably increased in both of EBC1 and H1993 cell lines after acquisition of resistance, compared to that before acquisition of resistance.

Example 5: Overcoming a Resistance to an Anti-c-Met Antibody by PNCK-Dependent Dual Targeting Agent to c-Met and EGFR It was confirmed that the resistance in a L3-1Y/IgG2 resistant cells can be overcome using ME22S which exhibits PNCK-dependent anticancer effect. For this, each of EBC1 (JCRB 0820), H1993 (ATCC, CRL-5909), and resistance acquired cell lines (EBC1-Re7, H1993-Re9, and H1993-Re21) was seeded on 96-well plate at the amount of 5000 cells. 24 hours after, the cells were treated with each of L3-1Y/IgG2, ME22S, and Erbitux (# ET509081213, Merck) at the concentration of 16 nM. 72 hours after the antibody treatment, the number of the cells was measured by CellTiter Glo assay (Promega, G7573). This assay measures the number of living cells by measuring the amount of ATP which reflects a metabolism of viable cells. The CellTiter Glo assay includes a substrate which emits luminescence when it reacts with ATP in a cell. The number of living cells can be quantified by measuring the emitted luminescence.

Figure 6:
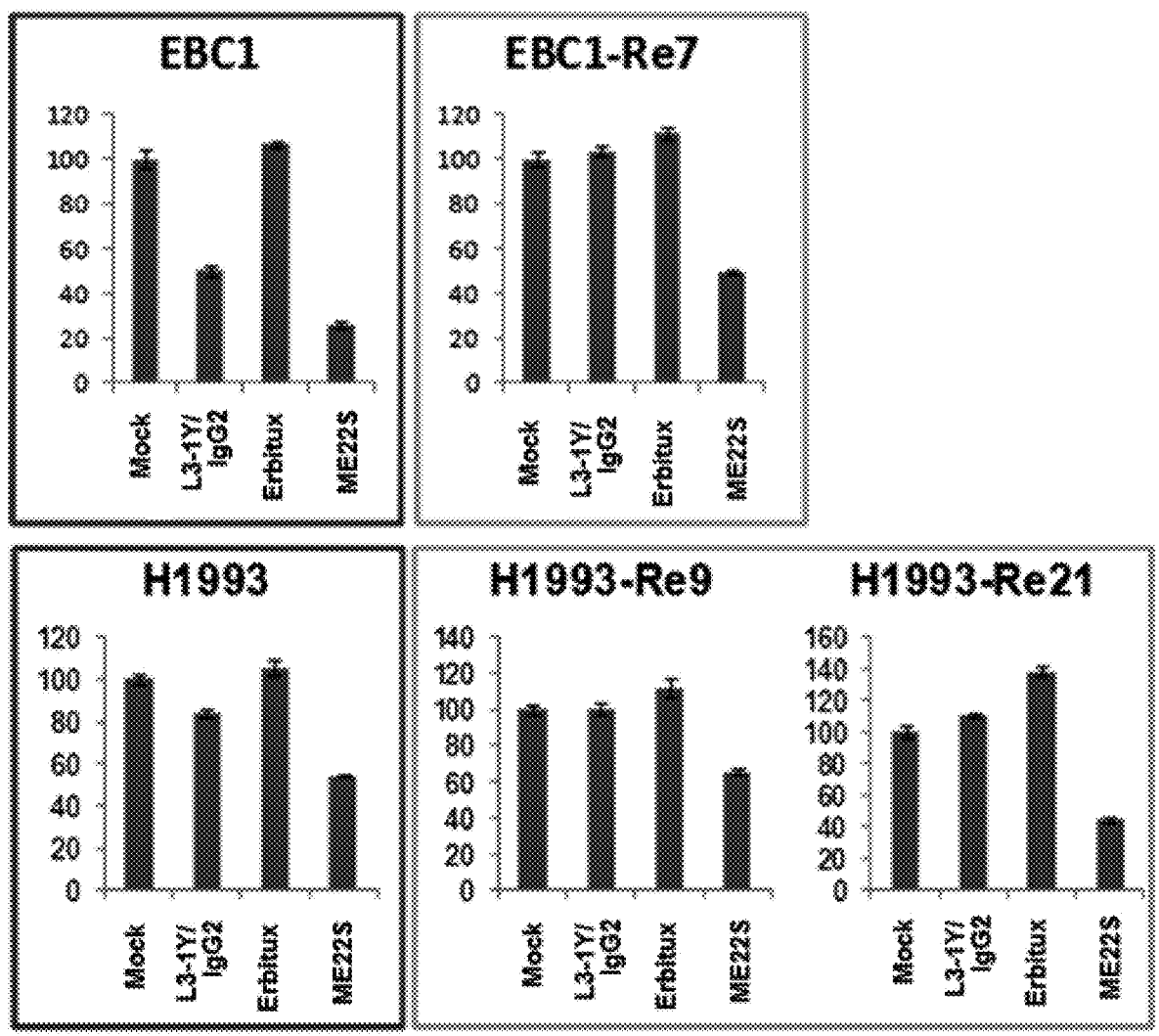
FIG. 6 demonstrates the effects of an anti-c-Met/anti-EGFR bispecific antibody (ME22S) on cell proliferation of EBC1 and H1993 cells that have acquired resistance to anti-c-Met antibodies.

The obtained results were shown in FIG. 6. In FIG. 6, Y axis shows the degree of cell proliferation relative to the degree of cell proliferation of a control (Mock) (100%). As shown in FIG. 6, L3-1Y/IgG2 has no effect of inhibiting the cell proliferation in L3-1Y/IgG2 resistance acquired cells, whereas ME22S maintain the effect of inhibiting the cell proliferation even in L3-1Y/IgG2 resistance acquired cells. these results indicate that in case the PNCK level is increased when acquiring a resistance to L3-1Y/IgG2, the resistance to L3-1Y/IgG2 can be overcome by sole administration of ME22S, which exhibits a PNCK-dependent effect.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating cancer associated with overexpression and/or abnormal activation of c-Met and/or EGFR in a patient, wherein the cancer is lung cancer, comprising:
   (I) selecting a patient for treatment with a dual-targeting agent that targets both c-Met and EGFR by a method comprising:
   (a) measuring PNCK protein level and/or PNCK gene expression level in a biological sample from a patient, and
   (b) selecting the patient for application of the dual-targeting agent that targets both c-Met and EGFR when the PNCK protein level or the PNCK gene expression level in the biological sample is higher than that of a reference sample comprising lung cancer cells with an acquired resistance to a c-Met inhibitor; and
   (II) administering to the patient the dual-targeting agent that targets both c-Met and EGFR, wherein the dual-targeting agent that targets both c-Met and EGFR is an anti-c-Met/anti-EGFR bispecific antibody.

2. The method of claim 1, wherein
the dual-targeting agent that targets both c-Met and EGFR is an anti-c-Met/anti-EGFR bispecific antibody comprising:
a c-Met binding region and a EGFR binding region, wherein
the c-Met binding region is an anti-c-Met antibody or an antigen-binding fragment thereof which recognizes or binds to a polypeptide comprising 5 to 19 contiguous amino acid residues within the amino acid sequence of SEQ ID NO: 71 and wherein the polypeptide comprises at least the amino sequence of SEQ ID NO: 73,
and the EGFR binding region comprises:
a) an anti-EGFR antibody or an antigen-binding fragment thereof comprising
a CDR-H1 comprising the amino acid sequence of SEQ ID NO: 109, a CDR-H2 comprising the amino acid sequence of SEQ ID NO: 110, and a CDR-H3 comprising the amino acid sequence of SEQ ID NO: 111; and
a CDR-L1 comprising the amino acid sequence of SEQ ID NO: 112, a CDR-L2 comprising the amino acid sequence of SEQ ID NO: 113, and a CDR-L3 comprising the amino acid sequence of SEQ ID NO: 114;

b) an anti-c-EGFR antibody comprising cetuximab or panitumumab, or c) an anti-EGFR antibody comprising a heavy chain variable region of SEQ ID NO: 121, and a light chain variable region of SEQ ID NO: 123, or an antigen-binding fragment thereof; or an anti-EGFR antibody comprising a heavy chain variable region of SEQ ID NO: 125, and a light chain variable region of SEQ ID NO: 126, or an antigen-binding fragment thereof.

3. The method of claim 1, wherein the anti-c-Met/anti-EGFR bispecific antibody comprises an anti-c-Met antibody or an antigen-binding fragment thereof comprising:
   (a) a CDR-H1 comprising the amino acid sequence of SEQ ID NO: 4; (b) a CDR-H2 comprising the amino acid sequence of SEQ ID NO: 5, the amino acid sequence of SEQ ID NO: 2, or an amino acid sequence comprising 8-19 consecutive amino acids within the amino acid sequence of SEQ ID NO: 2 comprising amino acid residues from the $3^{rd}$ to $10^{th}$ positions of the amino acid sequence of SEQ ID NO: 2; and (c) a CDR-H3 comprising the amino acid sequence of SEQ ID NO: 6, the amino acid sequence of SEQ ID NO: 85, or an amino acid sequence comprising 6-13 consecutive amino acids within the amino acid sequence of SEQ ID NO: 85 comprising amino acid residues from the $1^{st}$ to $6^{th}$ positions of the amino acid sequence of SEQ ID NO: 85; and
   (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, the amino acid sequence of SEQ ID NO: 15, the amino acid sequence of SEQ ID NO: 86, or an amino acid sequence comprising 9-17 consecutive amino acids within the amino acid sequence of SEQ ID NO: 89 comprising amino acid residues from the $1^{st}$ to $9^{th}$ positions of the amino acid sequence of SEQ ID NO: 89.

4. The method of claim 1, wherein the anti-c-Met/anti-EGFR bispecific antibody comprises an anti-EGFR antibody or antigen-binding fragment thereof comprising a heavy chain variable region comprising SEQ ID NO: 115 or SEQ ID NO: 117, a light chain variable region comprising SEQ ID NO: 116 or SEQ ID NO: 118, or a combination thereof.

5. The method of claim 1, wherein the anti-c-Met/anti-EGFR bispecific antibody comprises an anti-c-Met antibody and an antigen-binding fragment of an anti-EGFR antibody or anti-EGFR DARPin, which is linked to the C-terminus of the anti-c-Met antibody.

6. The method of claim 1, wherein the cancer is resistant to treatment with a c-Met inhibitor.

7. The method of claim 1, further comprising administering at least one selected from the group consisting of PNCK protein, PNCK gene, a recombinant vector containing the PNCK gene, and a recombinant cell comprising the PNCK gene or the recombinant vector.

8. A method of treating a cancer in a subject, comprising administering a dual-targeting agent that targets both c-Met and EGFR and at least one selected from the group consisting of PNCK protein, PNCK gene, a recombinant vector containing the PNCK gene, and a recombinant cell comprising the PNCK gene or the recombinant vector, to the subject, wherein the cancer is lung cancer.

9. The method of claim 8, wherein the cancer is resistant to treatment with a c-Met inhibitor and/or a dual-targeting agent that targets both c-Met and EGFR.

10. A method of treating cancer associated with overexpression and/or abnormal activation of c-Met and/or EGFR in a patient, wherein the cancer is lung cancer, comprising:
(I) selecting a patient for treatment with a dual-targeting agent that targets both c-Met and EGFR by a method comprising:
   (a) measuring PNCK protein level and/or PNCK gene expression level in a biological sample from a patient, and
   (b) selecting the patient for application of the dual-targeting agent that targets both c-Met and EGFR when the PNCK protein level or the PNCK gene expression level in the biological sample is higher than that of a reference sample comprising lung cancer cells with an acquired resistance to a c-Met inhibitor; and
(II) administering to the patient the dual-targeting agent that targets both c-Met and EGFR, wherein the dual-targeting agent that targets both c-Met and EGFR comprises:
(a) a c-Met binding region comprising:
a CDR-H1 comprising the amino acid sequence of SEQ ID NO: 4; a CDR-H2 comprising the amino acid sequence of SEQ ID NO: 5, the amino acid sequence of SEQ ID NO: 2, or an amino acid sequence comprising 8-19 consecutive amino acids within the amino acid sequence of SEQ ID NO: 2 comprising amino acid residues from the $3^{rd}$ to $10^{th}$ positions of the amino acid sequence of SEQ ID NO: 2;
a CDR-H3 comprising the amino acid sequence of SEQ ID NO: 6, the amino acid sequence of SEQ ID NO: 85, or an amino acid sequence comprising 6-13 consecutive amino acids within the amino acid sequence of SEQ ID NO: 85 comprising amino acid residues from the $1^{st}$ to $6^{th}$ positions of the amino acid sequence of SEQ ID NO: 85;
a CDR-L1 comprising the amino acid sequence of SEQ ID NO: 7; a CDR-L2 comprising the amino acid sequence of SEQ ID NO: 8, and
a CDR-L3 comprising the amino acid sequence of SEQ ID NO: 9, the amino acid sequence of SEQ ID NO: 15, the amino acid sequence of SEQ ID NO: 86, or an amino acid sequence comprising 9-17 consecutive amino acids within the amino acid sequence of SEQ ID NO: 89 comprising amino acid residues from the $1^{st}$ to $9^{th}$ positions of the amino acid sequence of SEQ ID NO: 89; and
(b) an EGFR binding region comprising:
an anti-EGFR antibody or an antigen-binding fragment thereof comprising a CDR-H1 comprising the amino acid sequence of SEQ ID NO: 109, a CDR-H2 comprising the amino acid sequence of SEQ ID NO: 110, a CDR-H3 comprising the amino acid sequence of SEQ ID NO: 111; a CDR-L1 comprising the amino acid sequence of SEQ ID NO: 112, a CDR-L2 comprising the amino acid sequence of SEQ ID NO: 113, and a CDR-L3 comprising the amino acid sequence of SEQ ID NO: 114;
or an anti-c-EGFR antibody comprising cetuximab or panitumumab,
or an anti-EGFR antibody comprising a heavy chain variable region of SEQ ID NO: 121, and a light chain variable region of SEQ ID NO: 123, or an antigen-binding fragment thereof;
or an anti-EGFR antibody comprising a heavy chain variable region of SEQ ID NO: 125, and a light chain variable region of SEQ ID NO: 126, or an antigen-binding fragment thereof
or
an anti-EGFR DARPin comprising 1 to 10 units which are independently selected from SEQ ID NOs: 127 to 130.

* * * * *

SEQUENCE LISTING

<160> NUMBER OF SEQ ID NOS: 131

<210> SEQ ID NO 1
<211> LENGTH: 5

```
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: X is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr
```

```
<400> SEQUENCE: 5

Arg Asn Xaa Xaa Asn Gly Xaa Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1               5                   10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
1               5
```

-continued

```
<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
```

<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ser Gln Ser Leu Leu Ala Ser
            20                  25                  30

```
Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
                100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Phe Thr Phe Gly Gln Gly Thr Lys Val Glu Ile
                100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
 1               5

<210> SEQ ID NO 24
```

```
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
1               5                   10                  15

Ala
```

```
<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone
```

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag gaaaggcact tgagtggttg ggttttatta gaaacaaagc taatggttac     240

```
acaacagagt acagtgcatc tgtgaagggt cggttcacca tctccagaga taattcccaa     300
agcatcctct atcttcaaat ggacaccctg agagctgagg acagtgccac ttattactgt     360
gcaagagata actggtttgc ttactggggc caagggactc tggtcactgt ctctgcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39

```
gaattcacta gtgattaatt cgccgccacc atggattcac aggcccaggt cctcatgttg      60
ctgctgctat cggtatctgg tacctgtgga cacttttga tgacccagtc tccatcctcc      120
ctgactgtgt cagcaggaga aaggtcact atgagctgca agtccagtca gagtctttta     180
gctagtggca accaaaataa ctacttggcc tggcaccagc agaaaccagg acgatctcct      240
aaaatgctga taatttgggc atccactagg gtatctggag tccctgatcg cttcataggc      300
agtggatctg ggacggattt cactctgacc atcaacagtg tgcaggctga agatctggct      360
gtttattact gtcagcagtc ctacagcgct ccgctcacgt tcggtgctgg gaccaagctg      420
gagctgaaac gtacggtggc tgcaccatct gtcttcatct cccgccatc tgatgagcag      480 ttgaaatctg gaactgcctc tgttgtgtgc ctgctgaata acttctatcc cagagaggcc      540
aaagtacagt ggaaggtgga taacgccctc caatcgggta actcccagga gagtgtcaca      600
gagcaggaca gcaaggacag cacctacagc ctcagcagca ccctgacgct gagcaaagca      660
gactacgaga aacacaaagt ctacgcctgc gaagtcaccc atcagggcct gagctcgccc      720
gtcacaaaga gcttcaacag gggagagtgt tgactcgag                             759
```

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy
<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
```

```
                225                 230                 235                 240
        Phe Leu Phe Pro Pro Lys Pro Lys Asp Thr Leu Met Ile Ser Arg Thr
                            245                 250                 255

Pro Glu Val Thr Cys Val Val Val Asp Val Ser His Glu Asp Pro Glu
                        260                 265                 270

Val Lys Phe Asn Trp Tyr Val Asp Gly Val Glu Val His Asn Ala Lys
                    275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Ala Lys Gly Gln Pro Arg Glu Pro Gln Val Tyr Thr Leu Pro
                    340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                    420                 425                 430

His Asn His Tyr Thr Gln Lys Ser Leu Ser Leu Ser Pro Gly Lys
                435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Thr Asp Tyr
                    20                  25                  30

Tyr Met Ser Trp Val Arg Gln Ala Pro Gly Lys Gly Leu Glu Trp Leu
                35                  40                  45

Gly Phe Ile Arg Asn Lys Ala Asn Gly Tyr Thr Thr Glu Tyr Ser Ala
            50                  55                  60

Ser Val Lys Gly Arg Phe Thr Ile Ser Arg Asp Asn Ser Lys Asn Ser
        65                  70                  75                  80

Leu Tyr Leu Gln Met Asn Ser Leu Arg Ala Glu Asp Thr Ala Val Tyr
                        85                  90                  95

Tyr Cys Ala Arg Asp Asn Trp Phe Ala Tyr Trp Gly Gln Gly Thr Leu
                    100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
```

```
                145                 150                 155                 160
        Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                        195                 200                 205

Thr Lys Val Asp Lys Lys Val Glu Pro Lys Ser Cys Asp Lys Thr His
                    210                 215                 220

Thr Cys Pro Pro Cys Pro Ala Pro Glu Leu Leu Gly Gly Pro Ser Val
        225                 230                 235                 240

Phe Leu Phe Pro Pro Lys Pro Lys Asp Thr Leu Met Ile Ser Arg Thr
                        245                 250                 255

Pro Glu Val Thr Cys Val Val Val Asp Val Ser His Glu Asp Pro Glu
                        260                 265                 270

Val Lys Phe Asn Trp Tyr Val Asp Gly Val Glu Val His Asn Ala Lys
                        275                 280                 285

Thr Lys Pro Arg Glu Glu Gln Tyr Asn Ser Thr Tyr Arg Val Val Ser
                    290                 295                 300

Val Leu Thr Val Leu His Gln Asp Trp Leu Asn Gly Lys Glu Tyr Lys
        305                 310                 315                 320

Cys Lys Val Ser Asn Lys Ala Leu Pro Ala Pro Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Arg Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
                        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                        420                 425                 430

His Asn His Tyr Thr Gln Lys Ser Leu Ser Leu Ser Pro Gly Lys
                    435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Thr Asp Tyr
                        20                  25                  30

Tyr Met Ser Trp Val Arg Gln Ala Pro Gly Lys Gly Leu Glu Trp Leu
                        35                  40                  45

Gly Phe Ile Arg Asn Lys Ala Asn Gly Tyr Thr Thr Glu Tyr Ser Ala
                    50                  55                  60

Ser Val Lys Gly Arg Phe Thr Ile Ser Arg Asp Asn Ser Lys Asn Thr
```

```
                65                  70                  75                  80
Leu Tyr Leu Gln Met Asn Ser Leu Arg Ala Glu Asp Thr Ala Val Tyr
                    85                  90                  95

Tyr Cys Ala Arg Asp Asn Trp Phe Ala Tyr Trp Gly Gln Gly Thr Leu
                    100                 105                 110

Val Thr Val Ser Ser Ala Ser Thr Lys Gly Pro Ser Val Phe Pro Leu
                    115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                    180                 185                 190

Leu Gly Thr Gln Thr Tyr Ile Cys Asn Val Asn His Lys Pro Ser Asn
                    195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light
```

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn

```
            130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
                20                  25                  30

Gly Asn Gln Asn Asn Tyr Leu Ala Trp Tyr Gln Gln Lys Pro Gly Gln
            35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
            210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46
```

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg gctggagtg ttgggctttt attagaaaca agctaacgg ttacaccaca       180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt ttgcttactg gggtcaagga accctggtca ccgtctcctc ggctagcacc     360
aagggcccat cggtcttccc cctggcaccc tcctccaaga gcacctctgg ggcacagcg     420 gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840

```
ggcgtggagg tgcataatgc aagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaccatctc caaagccaaa      1020 gggcagcccc gagaaccaca ggtgtacacc ctgcccccat cccgggagga gatgaccaag      1080
aaccaggtca gcctgacctg cctggtcaaa ggcttctatc ccagcgacat cgccgtggag      1140
tgggagagca atgggcagcc ggagaacaac tacaagacca cgcctcccgt gctggactcc      1200
gacggctcct tcttcctcta cagcaagctc accgtggaca gagcaggtg gcagcagggg       1260 aacgtcttct catgctccgt gatgcatgag gctctgcaca accactacac gcagaagagc      1320
ctctccctgt ctccgggtaa atgactcgag                                        1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc       60
tcctgtgcag cctctggatt caccttcact gactactaca tgagctgggt ccgccaggct      120
ccagggaagg gctggagtg gttgggcttt attagaaaca agctaacgg ttacaccaca        180 gaatacagtg cgtctgtgaa aggcagattc accatctcaa gagataattc aaagaactca      240
ctgtatctgc aaatgaacag cctgcgtgct gaggacacgg ccgtgtatta ctgtgctaga      300
gataactggt ttgcttactg gggtcaagga accctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt      660 gacaaaactc acacatgccc accgtgccca gcacctgaac tcctggggg accgtcagtc      720 ttcctcttcc cccaaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc aagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaccatctc caaagccaaa      1020 gggcagcccc gagaaccaca ggtgtacacc ctgcccccat cccgggagga gatgaccaag      1080
aaccaggtca gcctgacctg cctggtcaaa ggcttctatc ccagcgacat cgccgtggag      1140
tgggagagca atgggcagcc ggagaacaac tacaagacca cgcctcccgt gctggactcc      1200
gacggctcct tcttcctcta cagcaagctc accgtggaca gagcaggtg gcagcagggg       1260 aacgtcttct catgctccgt gatgcatgag gctctgcaca accactacac gcagaagagc      1320
ctctccctgt ctccgggtaa atgactcgag                                        1350
```

<210> SEQ ID NO 49
<211> LENGTH: 1350
<212> TYPE: DNA

<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggggctc actccgtttg      60
tcctgtgcag cttctggctt caccttcact gattactaca tgagctgggt gcgtcaggcc     120
ccgggtaagg gcctggaatg gttgggtttt attagaaaca aagctaatgg ttacacaaca     180
gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag      1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                     1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc      60
atcaactgca gtccagcca gagtctttta gctagcggca accaaaataa ctacttagct     120
tggcaccagc agaaaccagg acagcctcct aagatgctca tatttgggc atctacccgg     180
gtatccgggg tccctgaccg attcagtggc agcgggtctg ggacagattt cactctcacc     240
atcagcagcc tgcaggctga agatgtggca gtttattact gtcagcaatc ctatagtgct     300
cctctcacgt tcggaggcgg taccaaggtg gagatcaaac gtacggtggc tgcaccatct     360
gtcttcatct tcccgccatc tgatgagcag ttgaaatctg gaactgcctc tgttgtgtgc     420
ctgctgaata cttctatcc cagagaggcc aaagtacagt ggaaggtgga taacgccctc     480
caatcgggta actcccagga gagtgtcaca gagcaggaca gcaaggacag cacctacagc     540
```
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                            669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
gatattgtga tgacccagac tccactctcc ctgcccgtca cccctggaga gccggcctcc     60
atctcctgca gtccagtca gagtcttta gctagtggca accaaaataa ctacttggcc    120
tggcacctgc agaagccagg gcagtctcca cagatgctga tcatttgggc atccactagg   180
gtatctggag tcccagacag gttcagtggc agtgggtcag gcactgattt cacactgaaa   240
atcagcaggg tggaggctga ggatgttgga gtttattact gccagcagtc ctacagcgct   300
ccgctcacgt tcggacaggg taccaagctg gagctcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                            669

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52
gacatcgtga tgacccagtc tccagactcc ctggctgtgt ctctgggcga gagggccacc    60
atcaactgca gtccagcca gagtctttta gctagcggca accaaaataa ctacttagct   120
tggtaccagc agaaaccagg acagcctcct aagctgctca ttatttgggc atctacccgg   180
gtatccgggg tccctgaccg attcagtggc agcgggtctg ggacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tgactcgag                                                            669

<210> SEQ ID NO 53
<211> LENGTH: 669
<212> TYPE: DNA

<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc      60
atcacctgca agtccagtca gagtctttta gctagtggca accaaaataa ctacttggcc     120
tggcaccaac agaaaccagg aaaagctccg aaaatgctga ttatttgggc atccactagg     180
gtatctggag tcccttctcg cttctctgga tccgggtctg ggacggattt cactctgacc     240
atcagcagtc tgcagccgga agacttcgca acttattact gtcagcagtc ctacagcgct     300
ccgctcacgt tcggacaggg taccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaaagt ctacgcctgc     600
gaagtcaccc atcagggcct gagctcgccc gtcacaaaga gcttcaacag gggagagtgt     660
tgactcgag                                                             669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

```
Gly Leu Gly Gly Leu Gly Gly Gly Ser Gly Gly Gly Ser Gly
1               5                   10                  15

Gly Ser Ser Gly Val Gly Ser
            20
```

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg aatggttgg gtttcattag aaacaaggct     180
aacggttaca ctaccgaata ttctgcttct gttaagggta gattcaccat ttctagagac     240
aactctaaga cacccttgta cttgcaaatg aactccttga gagctgaaga tactgctgtt     300
tattactgcg ctagagataa ttggtttgct tattgggtc aaggtacttt ggttactgtt     360
tcttctggcc tcgggggcct cggaggagga ggtagtggcg aggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact ggcttggca tcaacaaaaa ccaggtaaag ctccaaagat gttgattatt     600
tgggcttcta ccagagtttc tggtgttcca tctagatttt ctggttctgg ttccggtact     660
```

| | | |
|---|---|---|
| gattttactt tgaccatttc atccttgcaa ccagaagatt tcgctactta ctactgtcaa | 720 | |
| caatcttact ctgctccatt gacttttggt caaggtacaa aggtcgaaat caagagagaa | 780 | |
| ttcggtaagc ctatccctaa ccctctcctc ggtctcgatt ctacgggtgg tggtggatct | 840 | |
| ggtggtggtg gttctggtgg tggtggttct caggaactga caactatatg cgagcaaatc | 900 | |
| ccctcaccaa ctttagaatc gacgccgtac tctttgtcaa cgactactat tttggccaac | 960 | |
| gggaaggcaa tgcaaggagt ttttgaatat acaaatcag taacgtttgt cagtaattgc | 1020 | |
| ggttctcacc cctcaacaac tagcaaaggc agccccataa acacacagta tgttttttga | 1080 | |
| gtttaaac | 1088 | |

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

| | | |
|---|---|---|
| acggattaga agccgccgag cgggtgacag ccctccgaag gaagactctc ctccgtgcgt | 60 | |
| cctcgtcttc accggtcgcg ttcctgaaac gcagatgtgc ctcgcgccgc actgctccga | 120 | |
| acaataaaga ttctacaata ctagctttta tggttatgaa gaggaaaaat tggcagtaac | 180 | |
| ctggccccac aaaccttcaa atgaacgaat caaattaaca accataggat gataatgcga | 240 | |
| ttagttttt agccttattt ctggggtaat taatcagcga agcgatgatt tttgatctat | 300 | |
| taacagatat ataaatgcaa aaactgcata accactttaa ctaatacttt caacattttc | 360 | |

```
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac atttttcaatt aagatgcagt   540 tacttcgctg ttttttcaata ttttctgtta ttgctagcgt tttagcagaa gttcaattgg   600
ttgaatctgg tggtggtttg gttcaaccag gtggttcttt gagattgtct tgtgctgctt   660
ctggttttac tttcaccgat tattacatgt cctgggttag acaagctcca ggtaaaggtt   720
tggaatggtt gggtttcatt agaaacaagg ctaacggtta cactaccgaa tattctgctt   780
ctgttaaggg tagattcacc atttctagag acaactctaa gaacaccttg tacttgcaaa   840
tgaactcctt gagagctgaa gatactgctg tttattactg cgctagagat aattggtttg   900
cttattgggg tcaaggtact ttggttactg tttcttctgg cctcgggggc ctcggaggag   960
gaggtagtgg cggaggaggc tccggtggat ccagcggtgt gggttccgat attcaaatga  1020
cccaatctcc atcttctttg tctgcttcag ttggtgatag agttaccatt acttgtaagt  1080
cctcccaatc tttgttggct tctggtaatc agaacaatta cttggcttgg catcaacaaa  1140
aaccaggtaa agctccaaag atgttgatta tttgggcttc taccagagtt tctggtgttc  1200
catctagatt ttctggttct ggttccggta ctgattttac tttgaccatt tcatccttgc  1260
aaccagaaga tttcgctact tactactgtc aacaatctta ctctgctcca ttgacttttg  1320
gtcaaggtac aaaggtcgaa atcaagagag aattcggtaa gcctatccct aaccctctcc  1380
tcggtctcga ttctacgggt ggtggtggat ctggtggtgg tggttctggt ggtggtggtt  1440
ctcaggaact gacaactata tgcgagcaaa tcccctcacc aactttagaa tcgacgccgt  1500
actctttgtc aacgactact attttggcca cgggaaggc aatgcaagga gttttttgaat  1560 attacaaatc agtaacgttt gtcagtaatt gcggttctca cccctcaaca actagcaaag  1620
gcagccccat aaacacacag tatgtttttt gagtttaaac ccgctgatct gataacaaca  1680
gtgtagatgt aacaaaatcg actttgttcc cactgtactt ttagctcgta caaaatacaa  1740 tatactttc atttctccgt aaacaacatg ttttcccatg taatatcctt ttctattttt   1800
cgttccgtta ccaactttac atatacttta tatagctatt cacttctata cactaaaaaa  1860
ctaagacaat tttaattttg ctgcctgcca tatttcaatt tgttataaat tcctataatt  1920
tatcctatta gtagctaaaa aaagatgaat gtgaatcgaa tcctaagaga attgggcaag  1980
tgcacaaaca atacttaaat aaatactact cagtaataac ctatttctta gcattttga   2040 cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa acatcctcc ttaggttgat   2460 tacgaaacac gccaaccaag tatttcggag tgcctgaact attttttatat gcttttacaa   2520 gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
```

```
cctcttggcc ctctcctttt cttttttcga ccgaatttct tgaagacgaa agggcctcgt    2820
gatacgccta tttttatagg ttaatgtcat gataataatg gtttcttagg acggatcgct    2880
tgcctgtaac ttacacgcgc ctcgtatctt ttaatgatgg ataaatttgg gaatttactc    2940
tgtgtttatt tattttatatg ttttgtattt ggattttaga aagtaaataa agaaggtaga    3000
agagttacgg aatgaagaaa aaaaaataaa caaaggttta aaaaatttca acaaaaagcg    3060
tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaaggt agtatttgtt    3240
ggcgatcccc ctagagtctt ttacatcttc ggaaaacaaa aactatttt tctttaattt    3300 cttttttac tttctatttt taatttatat atttatatta aaaaatttaa attataatta    3360
tttttatagc acgtgatgaa aaggacccag gtggcacttt tcggggaaat gtgcgcggaa    3420 ccccctatttg tttattttc taaatacatt caaatatgta tccgctcatg agacaataac    3480
cctgataaat gcttcaataa tattgaaaaa ggaagagtat gagtattcaa catttccgtg    3540
tcgcccttat tcccttttt gcggcatttt gccttcctgt ttttgctcac ccagaaacgc    3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca gtttactca tatatacttt agattgattt aaaacttcat ttttaattta    4440
aaaggatcta ggtgaagatc ctttttgata atctcatgac caaaatccct taacgtgagt    4500
tttcgttcca ctgagcgtca gaccccgtag aaaagatcaa aggatcttct tgagatcctt    4560 ttttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
```

```
ttttgtgatg ctcgtcaggg gggccgagcc tatggaaaaa cgccagcaac gcggccttt    5160 tacggttcct ggccttttgc tggccttttg ctcacatgtt ctttcctgcg ttatcccctg   5220
attctgtgga taaccgtatt accgcctttg agtgagctga taccgctcgc cgcagccgaa   5280
cgaccgagcg cagcgagtca gtgagcgagg aagcggaaga gcgcccaata cgcaaaccgc   5340
ctctccccgc gcgttggccg attcattaat gcagctggca cgacaggttt cccgactgga   5400
aagcgggcag tgagcgcaac gcaattaatg tgagttacct cactcattag gcaccccagg   5460
ctttacactt tatgcttccg gctcctatgt tgtgtggaat tgtgagcgga taacaatttc   5520
acacaggaaa cagctatgac catgattacg ccaagctcgg aattaaccct cactaaaggg   5580
aacaaaagct ggctagt                                                  5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
1               5                   10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

```
gaattcacta gtgattaatt cgccgccacc atggattcac aggcccaggt cctcatgttg   60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
tccgggtctg ggacggattt cactctgacc atcagcagtc tgcagccgga agacttcgca   360
acttattact gtcagcagtc ctacagccgc ccgtacacgt tcggacaggg taccaaggtg   420
gagatcaaac gtacg                                                    435
```

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59

```
gaattcacta gtgattaatt cgccgccacc atggattcac aggcccaggt cctcatgttg   60
ctgctgctat cggtatctgg tacctgtgga gatatccaga tgacccagtc cccgagctcc   120
ctgtccgcct ctgtgggcga tagggtcacc atcacctgca agtccagtca gagtctttta   180
gctagtggca accaaaataa ctacttggcc tggcaccaac agaaaccagg aaaagctccg   240
aaaatgctga ttatttgggc atccactagg gtatctggag tcccttctcg cttctctgga   300
```

```
tccgggtctg gacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                     435
```

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435
```

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61

```
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy
      chain of huAbF46-H4-A1, U6-HC7 hinge and constant region of
      human IgG1

<400> SEQUENCE: 62

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
```

```
            35                  40                  45
Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
                115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
                290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Glu Glu Met Thr Lys Asn Gln Val Ser Leu Thr Cys Leu Val
                370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460
```

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide consisting of heavy chain of huAbF46-H4-A1, U6-HC7 hinge and constant region of human IgG1

<400> SEQUENCE: 63

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta agcagagaa taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320
aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG1

<400> SEQUENCE: 64

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30
```

-continued

```
Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide consisting of heavy chain of huAbF46-H4-A1, human IgG2 hinge and constant region of human IgG1

<400> SEQUENCE: 65

```
gaattcgccg ccaccatgga atggagctgg gttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta agcagagaa taattccaaa   300
aacacactgt acctgcagat gaacagcctg cgtgctgagg acactgccgt ctattattgt   360
gctagagata actggtttgc ttactggggc caagggactc tggtcaccgt ctcctcggct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagaggaag   720
tgctgtgtgg agtgcccccc ctgcccagca cctgaactcc tggggggacc gtcagtcttc   780
ctcttccccc caaaacccaa ggacaccctc atgatctccc ggacccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggaggagat gaccaagaac  1140
caggtcagcc tgacctgcct ggtcaaaggc ttctatccca gcgacatcgc cgtggagtgg  1200
gagagcaatg ggcagccgga gaacaactac aagaccacgc tcccgtgct ggactccgac  1260
ggctccttct cctctacag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaatg actcgag                                      1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG2

<400> SEQUENCE: 66

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30
```

-continued

```
Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
            130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Asn Phe Gly Thr Gln Thr Tyr Thr Cys Asn Val Asp His Lys Pro Ser
210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
            275                 280                 285

Asn Trp Tyr Val Asp Gly Val Glu Val His Asn Ala Lys Thr Lys Pro
290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445
```

```
Tyr Thr Gln Lys Ser Leu Ser Leu Ser Pro Gly Lys
    450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactgggc caagggactc tggtcaccgt ctcctcggct    420
agcaccaagg gcccatcggt cttcccctg cgcccctgct ccaggagcac ctccgagagc    480
acagcggccc tgggctgcct ggtcaaggac tacttccccg aaccggtgac ggtgtcgtgg    540
aactcaggcg ctctgaccag cggcgtgcac accttccag ctgtcctaca gtcctcagga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttccccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag   1020
gtctccaaca aaggcctccc agcccccatc gagaaaacca tctccaaaac caagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1(H36Y) and human kappa constant region

<400> SEQUENCE: 68

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30
```

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
 50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                    85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and human kappa
      constant region

<400> SEQUENCE: 69
aattcactag tgattaattc gccgccacca tggattcaca ggcccaggtc ctcatgttgc     60
tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt ccctcctcgc ttctctggat    300
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgccctcc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                             758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
of huAbF46-H4-A1 and human kappa constant region

<400> SEQUENCE: 70

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Lys Ser Gln Ser
            35                  40                  45

Leu Leu Ala Ser Gly Asn Gln Asn Asn Tyr Leu Ala Trp His Gln Gln
        50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Thr Asp
                85                  90                  95

Phe Thr Leu Thr Ile Ser Ser Leu Gln Pro Glu Asp Phe Ala Thr Tyr
                100                 105                 110

Tyr Cys Gln Gln Ser Tyr Ser Arg Pro Tyr Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

```
Phe Ser Pro Gln Ile Glu Glu Pro Ser Gln Cys Pro Asp Cys Val Val
1               5                   10                  15

Ser Ala Leu
```

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

```
Pro Gln Ile Glu Glu Pro Ser Gln Cys Pro
1               5                   10
```

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

```
Glu Glu Pro Ser Gln
1               5
```

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
```

```
                85                  90                  95
Ser Tyr Ser Ala Pro Leu Thr Phe Gly Gly Gly Thr Lys Val Glu Ile
                    100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag aaaggcact tgagtggttg gttttatta gaaacaaagc taatggttac       240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
```

```
tacaagtgca aggtctccaa caaagccctc ccagccccca tcgagaaaac catctccaaa    1080 gccaagggc agccccgaga accacaggtg tacaccctgc ccccatcccg ggaggagatg     1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg    1260
gactccgacg gctccttctt cctctacagc aagctcaccg tggacaagag caggtggcag    1320 cagggaacg tcttctcatg ctccgtgatg catgaggctc tgcacaacca ctacacgcag     1380
aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga aaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

| | | | | | |
|---|---|---|---|---|---|
| atgaaggccc | ccgctgtgct | tgcacctggc | atcctcgtgc | tcctgtttac | cttggtgcag       60 |
| aggagcaatg | gggagtgtaa | agaggcacta | gcaaagtccg | agatgaatgt | gaatatgaag      120 |
| tatcagcttc | ccaacttcac | cgcggaaaca | cccatccaga | atgtcattct | acatgagcat      180 |
| cacattttcc | ttggtgccac | taactacatt | tatgttttaa | atgaggaaga | ccttcagaag      240 |
| gttgctgagt | acaagactgg | gcctgtgctg | aacacccag | attgtttccc | atgtcaggac      300 |
| tgcagcagca | agccaatttt | atcaggaggt | gtttggaaag | ataacatcaa | catggctcta      360 |
| gttgtcgaca | cctactatga | tgatcaactc | attagctgtg | gcagcgtcaa | cagagggacc      420 |
| tgccagcgac | atgtctttcc | ccacaatcat | actgctgaca | tacagtcgga | ggttcactgc      480 |
| atattctccc | cacagataga | agagcccagc | cagtgtcctg | actgtgtggt | gagcgccctg      540 |
| ggagccaaag | tcctttcatc | tgtaaaggac | cggttcatca | acttctttgt | aggcaatacc      600 |
| ataaattctt | cttatttccc | agatcatcca | ttgcattcga | tatcagtgag | aaggctaaag      660 |
| gaaacgaaag | atggttttat | gtttttgacg | gaccagtcct | acattgatgt | tttacctgag      720 |
| ttcagagatt | cttaccccat | taagtatgtc | catgcctttg | aaagcaacaa | ttttatttac      780 |
| ttcttgacgg | tccaaaggga | aactctagat | gctcagactt | tcacacaag | aataatcagg      840 |
| ttctgttcca | taaactctgg | attgcattcc | tacatggaaa | tgcctctgga | gtgtattctc      900 |
| acagaaaaga | gaaaaagag | atccacaaag | aaggaagtgt | ttaatatact | tcaggctgcg      960 |
| tatgtcagca | agcctggggc | ccagcttgct | agacaaatag | agccagcct | gaatgatgac     1020 |
| attcttttcg | gggtgttcgc | acaaagcaag | ccagattctg | ccgaaccaat | ggatcgatct     1080 |
| gccatgtgtg | cattccctat | caaatatgtc | aacgacttct | tcaacaagat | cgtcaacaaa     1140 |
| aacaatgtga | gatgtctcca | gcatttttac | ggacccaatc | atgagcactg | ctttaatagg     1200 |
| acacttctga | gaaattcatc | aggctgtgaa | gcgcgccgtg | atgaatatcg | aacagagttt     1260 |
| accacagctt | tgcagcgcgt | tgacttattc | atgggtcaat | tcagcgaagt | cctcttaaca     1320 |
| tctatatcca | ccttcattaa | aggagacctc | accatagcta | tcttgggac | atcagagggt     1380 |
| cgcttcatgc | aggttgtggt | ttctcgatca | ggaccatcaa | cccctcatgt | gaattttctc     1440 |
| ctggactccc | atccagtgtc | tccagaagtg | attgtggagc | atacattaaa | ccaaaatggc     1500 |
| tacacactgg | ttatcactgg | gaagaagatc | acgaagatcc | cattgaatgg | cttgggctgc     1560 |
| agacatttcc | agtcctgcag | tcaatgcctc | tctgccccac | cctttgttca | gtgtggctgg     1620 |
| tgccacgaca | aatgtgtgcg | atcggaggaa | tgcctgagcg | gacatggac | tcaacagatc     1680 |
| tgtctgcctg | caatctacaa | ggttttccca | aatagtgcac | cccttgaagg | agggacaagg     1740 |
| ctgaccatat | gtggctggga | ctttggattt | cggaggaata | taaatttga | ttttaaagaaa     1800 |
| actagagttc | tccttggaaa | tgagagctgc | accttgactt | taagtgagag | cacgatgaat     1860 |
| acattgaaat | gcacagttgg | tcctgccatg | aataagcatt | tcaatatgtc | cataattatt     1920 |
| tcaaatggcc | acgggacaac | acaatacagt | acattctcct | atgtggatcc | tgtaataaca     1980 |
| agtatttcgc | cgaaatacgg | tcctatggct | ggtggcactt | tacttacttt | aactggaaat     2040 |

| | | | | |
|---|---|---|---|---|
| tacctaaaca | gtgggaattc | tagacacatt | tcaattggtg | gaaaaacatg | tactttaaaa | 2100 |
| agtgtgtcaa | acagtattct | tgaatgttat | accccagccc | aaaccatttc | aactgagttt | 2160 |
| gctgttaaat | tgaaaattga | cttagccaac | cgagagacaa | gcatcttcag | ttaccgtgaa | 2220 |
| gatcccattg | tctatgaaat | tcatccaacc | aaatctttta | ttagtggtgg | gagcacaata | 2280 |
| acaggtgttg | ggaaaaacct | gaattcagtt | agtgtcccga | gaatggtcat | aaatgtgcat | 2340 |
| gaagcaggaa | ggaactttac | agtggcatgt | caacatcgct | ctaattcaga | gataatctgt | 2400 |
| tgtaccactc | cttccctgca | acagctgaat | ctgcaactcc | ccctgaaaac | caaagccttt | 2460 |
| ttcatgttag | atgggatcct | ttccaaatac | tttgatctca | tttatgtaca | taatcctgtg | 2520 |
| tttaagcctt | ttgaaaagcc | agtgatgatc | tcaatgggca | atgaaaatgt | actggaaatt | 2580 |
| aagggaaatg | atattgaccc | tgaagcagtt | aaaggtgaag | tgttaaaagt | tggaaataag | 2640 |
| agctgtgaga | atatacactt | acattctgaa | gccgttttat | gcacggtccc | caatgacctg | 2700 |
| ctgaaattga | acagcgagct | aaatatagag | tggaagcaag | caatttcttc | aaccgtcctt | 2760 |
| ggaaaagtaa | tagttcaacc | agatcagaat | ttcacaggat | tgattgctgg | tgttgtctca | 2820 |
| atatcaacag | cactgttatt | actacttggg | ttttcctgt | ggctgaaaaa | gagaaagcaa | 2880 |
| attaaagatc | tgggcagtga | attagttcgc | tacgatgcaa | gagtacacac | tcctcatttg | 2940 |
| gataggcttg | taagtgcccg | aagtgtaagc | ccaactacag | aaatggtttc | aaatgaatct | 3000 |
| gtagactacc | gagctacttt | tccagaagat | cagtttccta | attcatctca | gaacggttca | 3060 |
| tgccgacaag | tgcagtatcc | tctgacagac | atgtccccca | tcctaactag | tggggactct | 3120 |
| gatatatcca | gtccattact | gcaaaatact | gtccacattg | acctcagtgc | tctaaatcca | 3180 |
| gagctggtcc | aggcagtgca | gcatgtagtg | attgggccca | gtagcctgat | tgtgcatttc | 3240 |
| aatgaagtca | taggaagagg | gcattttggt | tgtgtatatc | atgggacttt | gttggacaat | 3300 |
| gatggcaaga | aaattcactg | tgctgtgaaa | tccttgaaca | gaatcactga | cataggagaa | 3360 |
| gtttcccaat | ttctgaccga | gggaatcatc | atgaaagatt | ttagtcatcc | caatgtcctc | 3420 |
| tcgctcctgg | gaatctgcct | gcgaagtgaa | gggtctccgc | tggtggtcct | accatacatg | 3480 |
| aaacatggag | atcttcgaaa | tttcattcga | aatgagactc | ataatccaac | tgtaaaagat | 3540 |
| cttattggct | ttggtcttca | gtagccaaa | ggcatgaaat | atcttgcaag | caaaaagttt | 3600 |
| gtccacagag | acttggctgc | aagaaactgt | atgctggatg | aaaaattcac | agtcaaggtt | 3660 |
| gctgattttg | gtcttgccag | agacatgtat | gataaagaat | actatagtgt | acacaacaaa | 3720 |
| acaggtgcaa | agctgccagt | gaagtggatg | gctttggaaa | gtctgcaaac | tcaaaagttt | 3780 |
| accaccaagt | cagatgtgtg | gtcctttggc | gtgctcctct | gggagctgat | gacaagagga | 3840 |
| gccccacctt | atcctgacgt | aaacaccttt | gatataactg | tttacttgtt | gcaagggaga | 3900 |
| agactcctac | aacccgaata | ctgcccagac | cccttatatg | aagtaatgct | aaaatgctgg | 3960 |
| caccctaaag | ccgaaatgcg | cccatccttt | tctgaactgg | tgtcccggat | atcagcgatc | 4020 |
| ttctctactt | tcattgggga | gcactatgtc | catgtgaacg | ctacttatgt | gaacgtaaaa | 4080 |
| tgtgtcgctc | cgtatccttc | tctgttgtca | tcagaagata | cgctgatga | tgaggtggac | 4140 |
| acacgaccag | cctccttctg | ggagacatca | | | | 4170 |

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Val Gly Asn Thr
130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Val Ser Arg Ser Gly Pro
```

```
                         405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
1               5                   10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
```

```
            325                 330                 335
Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
            355                 360                 365

Ser Met Gly Asn Glu Asn Val Leu Glu Ile Lys Gly Asn Asp Ile Asp
            370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
            435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
            35                  40                  45

Thr Glu Gly Ile Ile Met Lys Asp Phe Ser His Pro Asn Val Leu Ser
        50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
            115                 120                 125

Ala Ala Arg Asn Cys Met Leu Asp Glu Lys Phe Thr Val Lys Val Ala
        130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
            195                 200                 205

Asp Val Asn Thr Phe Asp Ile Thr Val Tyr Leu Leu Gln Gly Arg Arg
        210                 215                 220

Leu Leu Gln Pro Glu Tyr Cys Pro Asp Pro Leu Tyr Glu Val Met Leu
```

```
              225                 230                 235                 240
Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
                260                 265                 270

Val His Val Asn Ala Thr Tyr Val Asn Val Lys Cys Val Ala Pro Tyr
                275                 280                 285

Pro Ser Leu Leu Ser Ser Glu Asp Asn Ala Asp Asp Glu Val Asp Thr
            290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain
      of c-Met

<400> SEQUENCE: 82
ctacatgagc atcacatttt ccttggtgcc actaactaca tttatgtttt aaatgaggaa     60
gaccttcaga aggttgctga gtacaagact gggcctgtgc tggaacaccc agattgtttc    120
ccatgtcagg actgcagcag caaagccaat ttatcaggag tgtttggaa agataacatc     180 aacatggctc tagttgtcga cacctactat gatgatcaac tcattagctg tggcagcgtc    240
aacagaggga cctgccagcg acatgtcttt ccccacaatc atactgctga catacagtcg    300
gaggttcact gcatattctc cccacagata gaagagccca gccagtgtcc tgactgtgtg    360
gtgagcgccc tgggagccaa agtcctttca tctgtaaagg accggttcat caacttctt   420 gtaggcaata ccataaaattc ttcttatttc ccagatcatc cattgcattc gatatcagtg    480
agaaggctaa aggaaacgaa agatggtttt atgttttga cggaccagtc ctacattgat    540
gttttacctg agttcagaga ttcttacccc attaagtatg tccatgcctt tgaaagcaac    600 aattttatt acttcttgac ggtccaaagg gaaactctag atgctcagac ttttcacaca    660
agaataatca ggttctgttc cataaactct ggattgcatt cctacatgga aatgcctctg    720
gagtgtattc tcacagaaaa gagaaaaaag agatccacaa gaaggaagt gtttaatata    780 cttcaggctg cgtatgtcag caagcctggg gcccagcttg ctagacaaat aggagccagc    840
ctgaatgatg acattctttt cggggtgttc gcacaaagca agccagattc tgccgaacca    900
atggatcgat ctgccatgtg tgcattccct atcaaatatg tcaacgactt cttcaacaag    960
atcgtcaaca aaaacaatgt gagatgtctc cagcattttt acggacccaa tcatgagcac   1020
tgctttaata ggacacttct gagaaattca tcaggctgtg aagcgcgccg tgatgaatat   1080
cgaacagagt ttaccacagc tttgcagcgc gttgacttat tcatgggtca attcagcgaa   1140
gtcctcttaa catctatatc caccttcatt aaaggagacc tcaccatagc taatcttggg   1200
acatcagagg gtcgcttcat gcaggttgtg gtttctcgat caggaccatc aaccctcat   1260 gtgaattttc tcctggactc ccatccagtg tctccagaag tgattgtgga gcatacatta    1320
aaccaaaatg gc                                                        1332

<210> SEQ ID NO 83
<211> LENGTH: 1299
<212> TYPE: DNA
<213> ORGANISM: Artificial Sequence
```

<220> FEATURE:
<223> OTHER INFORMATION: Synthetic polynucleotide encoding PSI-IPT
    domain of c-Met

<400> SEQUENCE: 83

```
tacacactgg ttatcactgg gaagaagatc acgaagatcc cattgaatgg cttgggctgc    60
agacatttcc agtcctgcag tcaatgcctc tctgccccac cctttgttca gtgtggctgg   120
tgccacgaca aatgtgtgcg atcggaggaa tgcctgagcg ggacatggac tcaacagatc   180
tgtctgcctg caatctacaa ggttttccca aatagtgcac cccttgaagg agggacaagg   240
ctgaccatat gtggctggga ctttggattt cggaggaata taaatttga tttaaagaaa    300
actagagttc tccttggaaa tgagagctgc accttgactt taagtgagag cacgatgaat   360
acattgaaat gcacagttgg tcctgccatg aataagcatt tcaatatgtc cataattatt   420
tcaaatggcc acgggacaac acaatacagt acattctcct atgtggatcc tgtaataaca   480
agtatttcgc cgaaatacgg tcctatggct ggtggcactt tacttacttt aactggaaat   540
tacctaaaca gtgggaattc tagacacatt tcaattggtg aaaaacatg tactttaaaa    600
agtgtgtcaa acagtattct tgaatgttat accccagccc aaaccatttc aactgagttt   660
gctgttaaat tgaaaattga cttagccaac cgagagacaa gcatcttcag ttaccgtgaa   720
gatcccattg tctatgaaat tcatccaacc aaatctttta ttagtggtgg gagcacaata   780
acaggtgttg ggaaaaacct gaattcagtt agtgtcccga gaatggtcat aaatgtgcat   840
gaagcaggaa ggaactttac agtggcatgt caacatcgct ctaattcaga gataatctgt   900
tgtaccactc cttccctgca acagctgaat ctgcaactcc ccctgaaaac caaagccttt   960
ttcatgttag atgggatcct ttccaaatac tttgatctca tttatgtaca taatcctgtg  1020
tttaagcctt ttgaaaagcc agtgatgatc tcaatgggca atgaaaatgt actggaaatt  1080
aagggaaatg atattgaccc tgaagcagtt aaaggtgaag tgttaaaagt tggaaataag  1140
agctgtgaga atatacactt acattctgaa gccgttttat gcacggtccc caatgacctg  1200
ctgaaattga acagcgagct aaatatagag tggaagcaag caatttcttc aacgtccttc   1260
ggaaaagtaa tagttcaacc agatcagaat ttcacagga                          1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain
    of c-Met

<400> SEQUENCE: 84

```
gtgcatttca atgaagtcat aggaagaggg cattttggtt gtgtatatca tgggactttg    60
ttggacaatg atggcaagaa aattcactgt gctgtgaaat ccttgaacag aatcactgac   120
ataggagaag tttcccaatt tctgaccgag ggaatcatca tgaaagattt tagtcatccc   180
aatgtcctct cgctcctggg aatctgcctg cgaagtgaag gtctccgct ggtggtccta   240
ccatacatga acatggagaa tcttcgaaat ttcattcgaa atgagactca taatccaact   300
gtaaaagatc ttattggctt tggtcttcaa gtagccaaag catgaaata tcttgcaagc   360
aaaaagtttg tccacagaga cttggctgca agaaactgta tgctggatga aaaattcaca   420
gtcaaggttg ctgattttgg tcttgccaga gacatgtatg ataaagaata ctatagtgta   480
cacaacaaaa caggtgcaaa gctgccagtg aagtggatgg cttgggaaag tctgcaaact   540
```

```
caaaagttta ccaccaagtc agatgtgtgg tcctttggcg tgctcctctg ggagctgatg      600
acaagaggag ccccaccttc tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatccttt  ctgaactggt gtcccggata      780
tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg gagacatca                             939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
1               5                   10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88

```
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110
```

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

```
<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of
      anti c-Met humanized antibody(huAbF46-H4)

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45
```

```
Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110
```

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

```
Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Ala Ser
            20                  25                  30
Gly Asn Gln Asn Asn Tyr Leu Ala Trp His Gln Gln Lys Pro Gly Lys
        35                  40                  45
Ala Pro Lys Met Leu Ile Ile Trp Ala Ser Thr Arg Val Ser Gly Val
    50                  55                  60
Pro Asp Arg Phe Ile Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Ser Tyr Ser Ala Pro Leu Thr Phe Gly Gln Gly Thr Lys Leu Glu Ile
            100                 105                 110
```
Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

```
Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Ala Ser
            20                  25                  30
Gly Asn Gln Asn Asn Tyr Leu Ala Trp His Gln Gln Lys Pro Gly Lys
        35                  40                  45
Ala Pro Lys Met Leu Ile Ile Trp Ala Ser Thr Arg Val Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Ser Tyr Ser Ala Pro Leu Thr Phe Gly Gln Gly Thr Lys Leu Glu Ile
            100                 105                 110
```
Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro

```
1               5                    10
```

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

```
Glu Pro Lys Ser Cys Asp Cys His Cys Pro Pro Cys Pro
1               5                    10
```

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

```
Glu Arg Lys Cys Cys Val Glu Cys Pro Pro Cys Pro
1               5                    10
```

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

```
Glu Pro Arg Asp Cys Gly Cys Lys Pro Cys Pro Pro Cys Pro
1               5                    10
```

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

```
Glu Lys Cys Asp Lys Thr His Thr Cys Pro Pro Cys Pro
1               5                    10
```

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

```
Glu Pro Lys Ser Cys Asp Lys Thr His Thr Cys Pro Pro Cys Pro
1               5                    10                   15
```

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

```
Lys Ser Ser Gln Ser Leu Leu Ala Trp Gly Asn Gln Asn Asn Tyr Leu
1               5                    10                   15
```

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp

```
                165                 170                 175
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 5
<212> TYPE: PRT
<213> ORGANISM: Artificial Sequence
<220> FEATURE:
<223> OTHER INFORMATION: Synthetic CDR-H1 of anti-EGFR scFv

<400> SEQUENCE: 109

Asn Tyr Asp Met Ser
1               5

<210> SEQ ID NO 110
<211> LENGTH: 17
<212> TYPE: PRT
<213> ORGANISM: Artificial Sequence
<220> FEATURE:
<223> OTHER INFORMATION: Synthetic CDR-H2 of anti-EGFR scFv

<400> SEQUENCE: 110

Gly Ile Ser His Ser Ser Gly Ser Lys Tyr Tyr Ala Asp Ser Val Lys
1               5                   10                  15

Gly

<210> SEQ ID NO 111
<211> LENGTH: 13
<212> TYPE: PRT
<213> ORGANISM: Artificial Sequence
<220> FEATURE:
<223> OTHER INFORMATION: Synthetic CDR-H3 of anti-EGFR scFv

<400> SEQUENCE: 111

Lys Asp Ala Thr Pro Arg Pro Leu Lys Pro Phe Asp Tyr
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic CDR-L1 of anti-EGFR scFv

<400> SEQUENCE: 112

Thr Gly Ser Ser Ser Asn Ile Gly Asn Asn Asp Val Ser
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Synthetic CDR-L2 of anti-EGFR scFv

<400> SEQUENCE: 113

Asp Asp Asn Lys Arg Pro Ser
1               5
```

-continued

```
<210> SEQ ID NO 114
<211> LENGTH: 9
<212> TYPE: PRT
<213> ORGANISM: Artificial Sequence
<220> FEATURE:
<223> OTHER INFORMATION: Synthetic CDR-L3 of anti-EGFR scFv

<400> SEQUENCE: 114

Gly Ser Trp Asp Ala Ser Leu Asn Ala
1               5

<210> SEQ ID NO 115
<211> LENGTH: 121
<212> TYPE: PRT
<213> ORGANISM: Artificial Sequence
<220> FEATURE:
<223> OTHER INFORMATION: Synthetic Heavy chain variable region of
      anti-EGFR scFv

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Gly Ile Ser His Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Thr Pro Arg Pro Leu Lys Pro Phe Tyr Trp Gly
            100                 105                 110

Gln Gly Thr Leu Val Thr Val Ser Ser
        115                 120

<210> SEQ ID NO 116
<211> LENGTH: 111
<212> TYPE: PRT
<213> ORGANISM: Artificial Sequence
<220> FEATURE:
<223> OTHER INFORMATION: Synthetic Light chain variable region of
      anti-EGFR scFv

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Gly Gly Thr Lys Leu Thr Val Leu Gly
            100                 105                 110
```

```
<210> SEQ ID NO 117
<211> LENGTH: 121
<212> TYPE: PRT
<213> ORGANISM: Artificial Sequence
<220> FEATURE:
<223> OTHER INFORMATION: Synthetic heavy chain variable region of
      anti-EGFR antibody (modified)

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Cys Leu Glu Trp Val
        35                  40                  45

Ser Gly Ile Ser His Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120

<210> SEQ ID NO 118
<211> LENGTH: 111
<212> TYPE: PRT
<213> ORGANISM: Artificial Sequence
<220> FEATURE:
<223> OTHER INFORMATION: Synthetic light chain variable region of
      anti-EGFR antibody (modified)

<400> SEQUENCE: 118

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Ala Ser Leu
                85                  90                  95

Asn Ala Tyr Val Phe Gly Cys Gly Thr Lys Leu Thr Val Leu Gly
            100                 105                 110

<210> SEQ ID NO 119
<211> LENGTH: 363
<212> TYPE: DNA
<213> ORGANISM: Artificial Sequence
<220> FEATURE:
<223> OTHER INFORMATION: Synthetic coding nucleotide sequence of heavy
      chain variable region of anti-EGFR antibody

<400> SEQUENCE: 119
gaggtgcagc tgttggagtc tgggggaggc ttggtacagc ctggggggtc cctgagactc    60
```

```
tcctgtgcag cctctggatt cacctttagc aattatgata tgagctgggt ccgccaggct    120
ccagggaagg ggctggagtg ggtctcaggg atctctcata gtagtggtag taaatattac    180
gctgattctg taaaaggtcg gttcaccatc tccagagaca attccaagaa cacgctgtat    240
ctgcaaatga acagcctgag agccgaggac acggccgtgt attactgtgc gaaagatgct    300
actccgcgtc cgctgaagcc tttcgactac tggggccagg gtacactggt caccgtgagc    360
tca                                                                  363
```

<210> SEQ ID NO 120
<211> LENGTH: 333
<212> TYPE: DNA
<213> ORGANISM: Artificial Sequence
<220> FEATURE:
<223> OTHER INFORMATION: Synthetic coding nucleotide sequence of light
      chain variable region of anti-EGFR antibody

<400> SEQUENCE: 120

```
cagtctgtgc tgactcagcc accctcagcg tctgggaccc ccgggcagag ggtcaccatc    60
tcttgtactg gctcttcatc taatattggc aataatgatg tctcctggta ccagcagctc    120
ccaggaacgg cccccaaact cctcatctat gatgataata gcggccaag cggggtccct    180 gaccgattct ctggctccaa atctggcacc tcagcctccc tggccatcag tgggctccgg    240
tccgaggatg aggctgatta ttactgtggt cttgggatgc tagcctgaa tgcttatgtc    300 ttcggcggag gcaccaagct gacggtccta ggc                                 333
```

<210> SEQ ID NO 121
<211> LENGTH: 120
<212> TYPE: PRT
<213> ORGANISM: Artificial Sequence
<220> FEATURE:
<223> OTHER INFORMATION: Synthetic heavy-chain variable region of
      anti-EGFR antibody

<400> SEQUENCE: 121

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120
```

<210> SEQ ID NO 122
<211> LENGTH: 360
<212> TYPE: DNA
<213> ORGANISM: Artificial Sequence
<220> FEATURE:
<223> OTHER INFORMATION: Synthetic DNA encoding heavy-chain variable
      region of anti-EGFR antibody

<400> SEQUENCE: 122

```
caggtgcagc tggtgcagtc tggggctgag gtgaagaagc ctgggtcctc ggtgaaggtc    60
tcctgcaagg cctctggttt cacattcact gactacaaga tacactgggt gcgacaggcc   120
cctggacaag ggctcgagtg gatgggatat ttcaaccctg acagcggtta tagtacctac   180
gcacagaagt tccagggcag ggtcaccatt accgcggaca aatccacgag cacagcctac   240
atggagctga gcagcctgag atctgaggac acggccgtgt attactgtgc gagactatcc   300
ccaggcggtt actatgttat ggatgcctgg ggccaaggga ccaccgtgac cgtctcctca   360
```

<210> SEQ ID NO 123
<211> LENGTH: 108
<212> TYPE: PRT
<213> ORGANISM: Artificial Sequence
<220> FEATURE:
<223> OTHER INFORMATION: Synthetic light-chain variable region of
      anti-EGFR antibody

<400> SEQUENCE: 123

```
Asp Ile Gln Met Thr Gln Ser Pro Ser Ser Leu Ser Ala Ser Val Gly
1               5                  10                  15
Asp Arg Val Thr Ile Thr Cys Arg Ala Ser Gln Gly Ile Asn Asn Tyr
            20                  25                  30
Leu Asn Trp Tyr Gln Gln Lys Pro Gly Lys Ala Pro Lys Arg Leu Ile
        35                  40                  45
Tyr Asn Thr Asn Asn Leu Gln Thr Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Phe Pro Thr
                85                  90                  95
Phe Gly Gln Gly Thr Lys Leu Glu Ile Lys Arg Thr
            100                 105
```

<210> SEQ ID NO 124
<211> LENGTH: 324
<212> TYPE: DNA
<213> ORGANISM: Artificial Sequence
<220> FEATURE:
<223> OTHER INFORMATION: Synthetic DNA encoding light-chain variable
      region of anti-EGFR antibody

<400> SEQUENCE: 124

```
gatatccaga tgacccagtc tccatcctcc ctgtctgcat ctgtcggaga ccgggtcacc    60
atcacctgcc gggcaagtca gggcattaac aattacttaa attggtacca gcagaagcca   120
gggaaagccc ctaagcgcct gatctataat accaacaact tgcagacagg cgtcccatca   180
aggttcagcg gcagtggatc cgggacagaa ttcactctca ccatcagcag cctgcagcct   240
gaagattttg ccacctatta ctgcttgcag cataatagtt ttcccacgtt tggccagggc   300
accaagctcg agatcaagcg tacg                                           324
```

<210> SEQ ID NO 125
<211> LENGTH: 120
<212> TYPE: PRT
<213> ORGANISM: Artificial Sequence
<220> FEATURE:
<223> OTHER INFORMATION: Synthetic modified heavy-chain variable region
      of anti-EGFR antibody

```
<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Cys Leu Glu Trp Met
        35                  40                  45

Gly Tyr Ile Asn Pro Asn Ser Gly Tyr Ser Thr Tyr Ala Ser Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 126
<211> LENGTH: 108
<212> TYPE: PRT
<213> ORGANISM: Artificial Sequence
<220> FEATURE:
<223> OTHER INFORMATION: Synthetic modified light-chain variable region
      of anti-EGFR antibody

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Glu Ala Thr Tyr Tyr Cys Leu Gln His Asn Ser Phe Pro Thr
                85                  90                  95

Phe Gly Gln Cys Thr Lys Leu Glu Ile Lys Arg Thr
            100                 105

<210> SEQ ID NO 127
<211> LENGTH: 153
<212> TYPE: PRT
<213> ORGANISM: Artificial Sequence
<220> FEATURE:
<223> OTHER INFORMATION: Synthetic anti-EGFR DARPin-01

<400> SEQUENCE: 127

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asp Asp
            20                  25                  30

Thr Trp Gly Trp Thr Pro Leu His Leu Ala Ala Tyr Gln Gly His Leu
        35                  40                  45

Glu Ile Val Glu Val Leu Leu Lys Asn Gly Ala Asp Val Asn Ala Tyr
    50                  55                  60
```

```
Asp Tyr Ile Gly Trp Thr Pro Leu His Leu Ala Ala Asp Gly His Leu
65                  70                  75                  80

Glu Ile Val Glu Val Leu Leu Lys Asn Gly Ala Asp Val Asn Ala Ser
                85                  90                  95

Asp Tyr Ile Gly Asp Thr Pro Leu His Leu Ala Ala His Asn Gly His
            100                 105                 110

Leu Glu Ile Val Glu Val Leu Leu Lys His Gly Ala Asp Val Asn Ala
        115                 120                 125

Gln Asp Lys Phe Gly Lys Thr Ala Phe Asp Ile Ser Ile Asp Asn Gly
    130                 135                 140

Asn Glu Asp Leu Ala Glu Ile Leu Gln
145                 150

<210> SEQ ID NO 128
<211> LENGTH: 154
<212> TYPE: PRT
<213> ORGANISM: Artificial Sequence
<220> FEATURE:
<223> OTHER INFORMATION: Synthetic Anti-EGFR DARPin-67

<400> SEQUENCE: 128

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Thr Asp
            20                  25                  30

Asn Asp Gly Asn Thr Pro Leu His Leu Ser Ala Trp Ile Gly His Leu
        35                  40                  45

Glu Ile Val Glu Val Leu Leu Lys His Gly Ala Asp Val Asn Ala Asp
50                  55                  60

Asp Leu Leu Gly Met Thr Pro Leu His Leu Ala Asp Thr Gly His
65                  70                  75                  80

Leu Glu Ile Val Glu Val Leu Leu Lys Tyr Gly Ala Asp Val Asn Ala
                85                  90                  95

Arg Asp Thr Arg Gly Lys Thr Pro Leu His Leu Ala Ala Arg Asp Gly
            100                 105                 110

His Leu Glu Ile Val Glu Val Leu Leu Lys His Asp Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150

<210> SEQ ID NO 129
<211> LENGTH: 154
<212> TYPE: PRT
<213> ORGANISM: Artificial Sequence
<220> FEATURE:
<223> OTHER INFORMATION: Synthetic Anti-EGFR DARPin-68

<400> SEQUENCE: 129

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Phe Asp
            20                  25                  30

Tyr Trp Gly Met Thr Pro Leu His Leu Ala Ala Asp Asn Gly His Leu
        35                  40                  45

Glu Ile Val Glu Val Leu Leu Lys His Gly Ala Asp Val Asn Ala Ser
```

```
                50                  55                  60

Asp Asn Phe Gly Phe Thr Pro Leu His Leu Ala Ala Phe Tyr Gly His
 65                  70                  75                  80

Leu Glu Ile Val Glu Val Leu Lys His Gly Ala Asp Val Asn Ala
                 85                  90                  95

Phe Asp Met Trp Gly Asn Thr Pro Leu His Leu Ala Ala Gln Asn Gly
                100                 105                 110

His Leu Glu Ile Val Glu Val Leu Leu Lys Asn Gly Ala Asp Val Asn
                115                 120                 125

Ala Gln Asp Lys Phe Gly Lys Thr Ala Phe Asp Ile Ser Ile Asp Asn
            130                 135                 140

Gly Asn Glu Asp Leu Ala Glu Ile Leu Gln
145                 150
```

<210> SEQ ID NO 130
<211> LENGTH: 187
<212> TYPE: PRT
<213> ORGANISM: Artificial Sequence
<220> FEATURE:
<223> OTHER INFORMATION: Synthetic Anti-EGFR DARpin-69

<400> SEQUENCE: 130

```
Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Asp Asp
                 20                  25                  30

Asn Ala Gly Arg Thr Pro Leu His Leu Ala Ala Asn Phe Gly His Leu
             35                  40                  45

Glu Ile Val Glu Val Leu Leu Lys Asn Gly Ala Asp Val Asn Ala Lys
 50                  55                  60

Gly His His Cys Asn Thr Pro Leu His Leu Ala Ala Trp Ala Gly His
 65                  70                  75                  80

Leu Glu Ile Val Glu Val Leu Leu Lys Tyr Gly Ala Asp Val Asn Ala
                 85                  90                  95

Asp Asp Asp Glu Gly Tyr Thr Pro Leu His Leu Ala Ala Asp Ile Gly
                100                 105                 110

Asp Leu Glu Ile Val Glu Val Leu Leu Lys Tyr Gly Ala Asp Val Asn
                115                 120                 125

Ala Trp Asp Met Tyr Gly Arg Thr Pro Leu His Leu Ala Ala Ser Ala
            130                 135                 140

Gly His Leu Glu Ile Val Glu Val Leu Leu Lys Tyr Gly Ala Asp Val
145                 150                 155                 160

Asn Ala Gln Asp Lys Phe Gly Lys Thr Ala Phe Asp Ile Ser Ile Asp
                165                 170                 175

Asn Gly Asn Glu Asp Leu Ala Glu Ile Leu Gln
            180                 185
```

<210> SEQ ID NO 131
<211> LENGTH: 114
<212> TYPE: PRT
<213> ORGANISM: Artificial Sequence
<220> FEATURE:
<223> OTHER INFORMATION: Synthetic light chain variable region of
      anti c-Met antibody

<400> SEQUENCE: 131

```
Asp Ile Gln Met Thr Gln Ser Pro Ser Ser Leu Ser Ala Ser Val Gly
 1               5                  10                  15
```

```
Asp Arg Val Thr Ile Thr Cys Lys Ser Ser Gln Ser Leu Leu Ala Ser
        20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```